(12) United States Patent
Sweeney et al.

(10) Patent No.: US 8,478,392 B2
(45) Date of Patent: Jul. 2, 2013

(54) RHYTHM DISCRIMINATION USING INFORMATION INDICATIVE OF LEAD MOTION

(75) Inventors: Robert J. Sweeney, Woodbury, MN (US); Allan C. Shuros, St. Paul, MN (US); Krzysztof Z. Siejko, Maple Grove, MN (US); David C. Olson, Eden Prairie, MN (US); Frank Ingle, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 87 days.

(21) Appl. No.: 13/168,481

(22) Filed: Jun. 24, 2011

(65) Prior Publication Data

US 2011/0319779 A1    Dec. 29, 2011

Related U.S. Application Data

(60) Provisional application No. 61/359,430, filed on Jun. 29, 2010.

(51) Int. Cl.
*A61B 5/04* (2006.01)

(52) U.S. Cl.
USPC ........................................................ 600/515

(58) Field of Classification Search
USPC ........................................................ 600/515
See application file for complete search history.

(56) References Cited

U.S. PATENT DOCUMENTS

| 3,012,192 | A | 12/1961 | Lion |
| 4,011,500 | A | 3/1977 | Pelletier et al. |
| 5,271,392 | A | 12/1993 | Ferek-Petric |
| 5,324,326 | A | 6/1994 | Lubin |
| 5,361,776 | A | 11/1994 | Samuelson et al. |
| 5,417,717 | A | 5/1995 | Salo et al. |
| 5,448,222 | A | 9/1995 | Harman |
| 5,554,177 | A | 9/1996 | Kieval et al. |
| 5,564,434 | A | 10/1996 | Halperin et al. |
| 5,693,074 | A | 12/1997 | Ferek-Petric |

(Continued)

FOREIGN PATENT DOCUMENTS

| EP | 0578748 B1 | 5/1996 |
| EP | 0670743 B1 | 12/2001 |

(Continued)

OTHER PUBLICATIONS

"U.S. Appl. No. 13/168,507, Non Final Office Action mailed Dec. 21, 12", 10 pgs.

(Continued)

*Primary Examiner* — George Manuel
(74) *Attorney, Agent, or Firm* — Schwegman Lundberg Woessner, P.A.

(57) ABSTRACT

Systems and methods for rhythm discrimination using the motion of an implantable lead are described. In an example, an implantable medical device can include a receiver circuit configured to be electrically coupled to an implantable lead and be configured to obtain information indicative of a movement of the implantable lead due at least in part to a motion of a heart. The device can include an arrhythmia detection circuit configured to determine an arrhythmia status using the information indicative of the movement of the implantable lead and an arrhythmia classification circuit configured to determine one or more of a location or a type of an arrhythmia, using the information indicative of the movement of the implantable lead, when the arrhythmia status indicates that an arrhythmia is occurring or has occurred.

24 Claims, 16 Drawing Sheets

U.S. PATENT DOCUMENTS

| | | | |
|---|---|---|---|
| 5,694,943 | A | 12/1997 | Brewer et al. |
| 5,897,577 | A | 4/1999 | Cinbis et al. |
| 5,899,927 | A | 5/1999 | Ecker et al. |
| 6,094,981 | A | 8/2000 | Hochstein |
| 6,285,898 | B1 | 9/2001 | Ben-Haim |
| 6,317,628 | B1 | 11/2001 | Linder et al. |
| 6,445,951 | B1 | 9/2002 | Mouchawar |
| 6,591,143 | B1 | 7/2003 | Ekwall |
| 6,869,404 | B2 | 3/2005 | Schulhauser et al. |
| 6,873,870 | B2 | 3/2005 | Ferek-Petric |
| 6,980,866 | B2 | 12/2005 | Yu et al. |
| 7,025,727 | B2 | 4/2006 | Brockway et al. |
| 7,035,684 | B2 | 4/2006 | Lee |
| 7,047,083 | B2 | 5/2006 | Gunderson et al. |
| 7,248,923 | B2 | 7/2007 | Maile et al. |
| 7,689,286 | B2 | 3/2010 | Pastore et al. |
| 7,787,946 | B2 * | 8/2010 | Stahmann et al. ............ 607/3 |
| 2005/0137636 | A1 | 6/2005 | Gunderson et al. |
| 2006/0282000 | A1 | 12/2006 | Zhang et al. |
| 2007/0299477 | A1 | 12/2007 | Kleckner et al. |
| 2008/0077333 | A1 | 3/2008 | Maxey et al. |
| 2008/0119750 | A1 | 5/2008 | Patangay et al. |
| 2008/0242976 | A1 | 10/2008 | Robertson et al. |
| 2008/0269820 | A1 | 10/2008 | Nilsson |
| 2009/0030334 | A1 | 1/2009 | Anderson et al. |
| 2009/0177110 | A1 | 7/2009 | Lyden et al. |
| 2009/0204163 | A1 | 8/2009 | Shuros et al. |
| 2009/0299432 | A1 | 12/2009 | Stadler et al. |
| 2010/0069768 | A1 | 3/2010 | Min et al. |
| 2010/0076279 | A1 | 3/2010 | Shuros et al. |
| 2010/0179421 | A1 | 7/2010 | Tupin |
| 2011/0319772 | A1 | 12/2011 | Ingle |
| 2011/0319776 | A1 | 12/2011 | Sweeney et al. |
| 2011/0319778 | A1 | 12/2011 | Sweeney et al. |
| 2011/0319782 | A1 | 12/2011 | Sweeney et al. |

FOREIGN PATENT DOCUMENTS

| | | |
|---|---|---|
| EP | 1469910 | 12/2006 |
| EP | 1515770 B1 | 6/2009 |
| WO | WO-95/03086 A2 | 2/1995 |
| WO | WO-95/27531 A | 10/1995 |
| WO | WO-2004/103458 A2 | 12/2004 |
| WO | WO-2005/089638 A1 | 9/2005 |
| WO | WO-2008/054261 A1 | 5/2008 |
| WO | WO-2009/058638 A1 | 5/2009 |
| WO | WO-2010/033190 A2 | 3/2010 |
| WO | WO-2012/005985 A2 | 1/2012 |
| WO | WO-2012/005985 A3 | 1/2012 |
| WO | WO-2012/005987 A2 | 1/2012 |
| WO | WO-2012/005987 A3 | 1/2012 |
| WO | WO-2012/005988 A2 | 1/2012 |
| WO | WO-2012/005988 A3 | 1/2012 |
| WO | WO-2012/005989 A2 | 1/2012 |
| WO | WO-2012/005989 A3 | 1/2012 |
| WO | WO-2012/005991 A2 | 1/2012 |
| WO | WO-2012/005991 A3 | 1/2012 |

OTHER PUBLICATIONS

"U.S. Appl. No. 13/168,531, Response filed Jan. 8, 2013 to Restriction Requirement mailed Dec. 21, 2012", 9 pgs.

"U.S. Appl. No. 13/168,531, Restriction Requirement mailed Dec. 21, 2012", 6 pgs.

"U.S. Appl. No. 13/168,547, Non Final Office Action mailed Dec. 11, 2012", 10 pgs.

"International Application Serial No. PCT/US2011/041834, International Preliminary Report on Patentability mailed Jan. 17, 2013", 7 pgs.

"International Application Serial No. PCT/US2011/041850, International Preliminary Report on Patentability mailed Jan. 17, 2013", 7 pgs.

"International Application Serial No. PCT/US2011/041854, International Preliminary Report on Patentability mailed Jan. 17, 2013", 6 pgs.

"International Application Serial No. PCT/US2011/041860, International Preliminary Report on Patentability mailed Jan. 17, 2013", 7 pgs.

"International Application Serial No. PCT/US2011/041868, International Preliminary Report on Patentability mailed Jan. 17, 2013", 7 pgs.

"Japanese Name Application Serial No. [Pending], Voluntary Amendment filed Dec. 27, 2012", With English Claims, 49 pgs.

"International Application Serial No. PCT/US2011/041834, International Search Report mailed Jan. 26, 2012", 3 pgs.

"International Application Serial No. PCT/US2011/041834, International Written Opinion mailed Jan. 26, 2012", 5 pgs.

"International Application Serial No. PCT/US2011/041850, International Search Report mailed Feb. 1, 2012", 4 pgs.

"International Application Seriai No. PCT/US2011/041850, International Written Opinion mailed Feb. 1, 2012", 5 pgs.

"International Application Serial No. PCT/US2011/041854, International Search Report Mailed Jan. 26, 2012", 4 pgs.

"International Application Serial No. PCT/US2011/041854, International Written Opinion Mailed Jan. 26, 2012", 4 pgs.

"International Application Serial No. PCT/US2011/041868, International Search Report mailed Jan. 26, 2012", 4 pgs.

"International Application Seriai No. PCT/US2011/041868, International Written Opinion mailed Jan. 26, 2012", 5 pgs.

"International Serial No. PCT/US2011/041860, International Search Report mailed Jan. 26, 2012", 4 pgs.

"International Serial No. PCT/US2011/041860, International Written Opinion mailed Jan. 26, 2012", 5 pgs.

"Lion's Twin-T Circuit Revisited", *IEEE Engineering in Medicine and Biology*, (Sep. 1992), 1-66.

Brusich, S., et al., "Cardiac Lead Used as Contractility Sensor: Animal Study", *HRS 2011, Innovators Poster Session—Esplanade Foyer Moscone South*, (May 6, 2011).

* cited by examiner

RHYTHM DISCRIMINATION USING INFORMATION INDICATIVE OF LEAD MOTION

CLAIM OF PRIORITY

This patent application claims the benefit of priority, under 35 U.S.C. Section 119(e), to Ingle U.S. Provisional Patent Application Ser. No. 61/359,430, entitled "Lead Motion Sensing Using Cable Microphonics," filed on Jun. 29, 2010, which is hereby incorporated by reference herein in its entirety.

CROSS REFERENCE TO RELATED APPLICATIONS

This patent application is related to:
(1) U.S. patent application Ser. No. 13/168,507;
(2) U.S. patent application Ser. No. 13/168,531; and
(3) U.S. patent application Ser. No. 13/168,547; each of which is hereby incorporated herein by reference in its respective entirety.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead. Examples of such devices can include cardiac function management (CFM) devices including one or more of implantable pacemakers, implantable cardioverter-defibrillators (ICDs), cardiac resynchronization therapy devices (CRTs), or one or more other devices. Such devices may include one or more electrodes coupled, such as via the implantable lead, to circuitry located on or within the IMD. Such circuitry can be configured to monitor electrical activity, such as to obtain information indicative of electrical activity of the heart.

A cardiac electrotherapy device to measure cardiac contractions using an elongated lead body that forms a high frequency transmission line is mentioned in U.S. Pat. No. 5,693,074 entitled "Cardiac Electrotherapy Device for Cardiac Contraction Measurement."

A time domain reflectometry impedance sensor for measuring body impedance along a lead or catheter implanted in a patient's cardiovascular system is mentioned in U.S. Pat. No. 5,361,776 entitled "Time Domain Reflectometer Impedance Sensor Method of Use and Implantable Cardiac Stimulator Using Same."

OVERVIEW

Generally, an IMD can obtain information indicative of cardiac activity such as by monitoring electrical signals. Such events can include heart chamber expansions or contractions, for example. By monitoring cardiac signals indicative of expansions or contractions, IMDs can detect an arrhythmia, such as an abnormally slow heart rate (a bradycardia), or an abnormally rapid heart rate (a tachyarrhythmia), among other arrhythmias. For example, a tachyarrhythmia can include a ventricular tachycardia (VT) or supraventricular tachycardia (SVT) (e.g., tachyarrhythmia originating outside the ventricles. Tachyarrhythmia can also be used generally, to describe rapid and irregular heart activity, such as fibrillation, including ventricular fibrillation (VF).

A ventricular tachyarrhythmia (e.g., ventricular fibrillation, ventricular tachycardia, etc.) can be potentially fatal if left untreated. During a ventricular tachyarrhythmia, the patient can rapidly lose consciousness. An implantable or external defibrillator can be used to convert such an arrhythmia back to a normal sinus rhythm, such as using an electrical shock therapy In contrast, tachyarrhythmias that occur in the atrial chambers of the heart are generally non-life threatening (though such arrhythmias can present a heightened risk of stroke or thrombo-embolism). Tachyarrhythmias that originate elsewhere from the ventricles can be referred to generally as supraventricular tachyarrhythmias (e.g., including atrial arrhythmias such as atrial tachycardia, atrial flutter, atrial fibrillation, etc.). Generally, the patient remains conscious during such supraventricular arrhythmias, and thus a shock therapy may be discouraged to avoid causing patient discomfort.

Thus, an IMD can be configured to detect an arrhythmia, or to classify an arrhythmia as ventricular in origin, or supraventricular in origin, such as to aid in guiding therapy (e.g., enabling or suppressing a cardiac shock therapy, or triggering initiation of an anti-tachyarrhythmia pacing (ATP) pacing therapy).

The present inventors have recognized, among other things, that mechanical information indicative of cardiac, blood, or vascular motion can be detected using a motion of one or more conductors electrically coupled to an ambulatory device, such as an IMD. Such information can be used by the IMD in one or more of detecting an arrhythmia, classifying the arrhythmia, or guiding therapy, in addition to using sensed cardiac electrical activity, or instead of using such sensed electrical activity. For example, the present inventors have also recognized that an implantable lead electrically and mechanically tethered to the IMD can provide information indicative of the motion of the lead, such as using one or more electrical measurements as described in the following examples, such as to detect cardiac, blood, or vascular motion. Such information indicative of motion can also be used to adjust therapy timing or other therapy parameters, or obtain information about the effectiveness of a cardiac therapy (e.g., electrostimulation), in addition to diagnosing one or more cardiac conditions. The present inventors have also recognized, among other things, that such information can be obtained via measurement of variation in electrical parameters corresponding to the motion of one or more therapy-conducting or activity-sensing conductors located on or within the lead assembly, without requiring a dedicated mechanical or acceleration sensor incorporated into the lead assembly.

In an example, an implantable medical device can include a receiver circuit configured to be electrically coupled to an implantable lead and be configured to obtain information indicative of a movement of the implantable lead due at least in part to a motion of a heart. The device can include an arrhythmia detection circuit configured to determine an arrhythmia status using the information indicative of the movement of the implantable lead and an arrhythmia classification circuit configured to determine one or more of a location or a type of an arrhythmia, using the information indicative of the movement of the implantable lead, when the arrhythmia status indicates that an arrhythmia is occurring or has occurred.

Example 1 can include subject matter (such as a system, a method, a means for performing acts, or a machine-readable medium including instructions that, when performed by the machine, cause the machine to perform acts, etc.) that can include an implantable medical device (IMD) that can include a receiver circuit, an arrhythmia detection circuit, and an arrhythmia classification circuit. The receiver circuit can be configured to be electrically coupled to an implantable lead and to obtain information indicative of a movement of the implantable lead due at least in part to a motion of a heart. The arrhythmia detection circuit can be configured to determine an arrhythmia status using the information indicative of the movement of the implantable lead. The arrhythmia classification circuit, can be coupled to the arrhythmia detection circuit and can be configured to determine one or more of a location or a type of an arrhythmia, using the information indicative of the movement of the implantable lead, in response to the arrhythmia detection circuit determining an arrhythmia status indicating that an arrhythmia is occurring or has occurred.

In Example 2, the subject matter of Example 1 can optionally be configured such that the arrhythmia classification circuit can determine the location of the arrhythmia.

In Example 3, the subject matter of Examples 1 and 2 can optionally be configured such that the arrhythmia classification circuit can determine the type of the arrhythmia.

In Example 4, the subject matter of Examples 1-3 can optionally include an excitation circuit configured to provide a non-tissue stimulating, non-therapeutic electrical excitation signal to the implantable lead, where the signal can include a time varying signal including a first range of frequencies.

In Example 5, the subject matter of Examples 1-4 can optionally be configured such that the information indicative of a movement of the implantable lead includes one or more of magnitude information, or phase information, corresponding to one or more frequencies included in the first range of frequencies. The magnitude information, or phase information can be determined at least in part using an electrical response signal provided by the implantable lead in response to the excitation signal and the movement of the implantable lead.

In Example 6, the subject matter of Examples 1-5 can optionally be configured such that one or more of the magnitude information or the phase information can include a time-varying portion corresponding to the movement of the implantable lead.

In Example 7, the subject matter of Examples 1-6 can optionally include an implantable lead configured to be located within or near the heart. The implantable lead can include an electrode configured to provide one or more of electrostimulation to the heart or to sense cardiac electrical activity.

In Example 8, the subject matter of Examples 1-7 can optionally be configured such that the implantable lead comprises a piezoelectric acoustic transducer configured to receive acoustic information indicative of the movement of the implantable lead, wherein the piezoelectric acoustic transducer can be coupled to a conductor included in the implantable lead.

In Example 9, the subject matter of Examples 1-8 can optionally be configured such that the arrhythmia classification circuit can determine one or more of an arrhythmia type or arrhythmia location using morphology information or interval information indicative of lead movement corresponding to successive cardiac cycles.

In Example 10, the subject matter of Examples 1-9 can optionally include a sensing circuit configured to obtain information indicative of cardiac electrical activity, where the sensing circuit can be coupled to the arrhythmia detection circuit. The arrhythmia detection circuit can optionally be configured to determine an arrhythmia status using the information indicative of the movement of the implantable lead and information obtained via the sensing circuit.

In Example 11, the subject matter of Examples 1-10 can optionally be configured such that the receiver circuit can be configured to obtain information indicative of lead motion from at least two different locations within or near the heart. The arrhythmia classification circuit can optionally be configured to determine the one or more of the type or location of the arrhythmia using information about the location of lead motion.

In Example 12, the subject matter of Examples 1-11 can optionally include a first lead located within or near a first location of the heart and a second lead located within or near a second location of the heart.

In Example 13, the subject matter of Examples 1-12 can optionally include a therapy generation circuit coupled to the arrhythmia classification circuit. The therapy generation circuit can optionally be configured to provide a therapy in response to information about at least one of the arrhythmia status or the location or the type of an arrhythmia.

In Example 14, the subject matter of Examples 1-13 can optionally be configured such that the therapy generation circuit can be inhibited from generating an arrhythmia therapy when the information about at least one of the arrhythmia status or the location or the type of an arrhythmia indicates that an arrhythmia, such as an ongoing arrhythmia, is one or more of supraventricular in origin or hemodynamically stable.

In Example 15, the subject matter of Examples 1-14 can optionally be configured such that the arrhythmia detection circuit can determine interval information about one or more time intervals between successive cardiac contractions; and wherein the arrhythmia detection circuit can determine an arrhythmia status using the interval information.

Example 16 can include, or can be combined with the subject matter of one or any combination of Examples 1-15 to optionally include, subject matter (such as an apparatus, a method, a means for performing acts, or a machine-readable medium including instructions that, when performed by the machine, cause the machine to obtain information indicative of a movement of an implantable lead electrically coupled to a receiver circuit included as a portion of the IMD, the movement due at least in part to a motion of a heart, to determine an arrhythmia status using the information indicative of the movement of an implantable lead, and to determine one or more of a location or a type of an arrhythmia, using the information indicative of the movement of the implantable lead, in response to the determined arrhythmia status indicating that an arrhythmia is occurring or has occurred.

In Example 17, the subject matter of Example 16 can optionally include instructions that, when executed by the processor, cause the IMD to determine a location of an arrhythmia, using the information indicative of the movement of the implantable lead, in response to the determination that an arrhythmia is occurring or has occurred.

In Example 18, the subject matter of one or any combination of Examples 16 or 17 can optionally include instructions that, when executed by the processor, cause the IMD to determine a type of an arrhythmia, using the information indicative of the movement of the implantable lead, in response to the determination that an arrhythmia is occurring or has occurred.

In Example 19, the subject matter of one or any combination of Examples 16-18 can optionally include instructions that, when executed by the processor, cause the IMD to determine interval information about one or more time intervals between successive cardiac contractions, and to determine an arrhythmia status using the interval information.

In Example 20, the subject matter of one or any combination of Examples 16-19 can optionally include instructions that, when executed by the processor, cause the IMD to determine one or more of an arrhythmia type or location using morphology information or interval information indicative of lead movement corresponding to successive cardiac cycles.

In Example 21, the subject matter of one or any combination of Examples 16-20 can optionally include instructions that, when executed by the processor, cause the IMD to obtain information indicative of cardiac electrical activity and to determine an arrhythmia status using the information indicative of the movement of the implantable lead and the information indicative of cardiac electrical activity obtained via the sensing circuit.

In Example 22, the subject matter of one or any combination of Examples 16-21 can optionally include instructions that, when executed by the processor, cause the IMD to provide a therapy, such as an arrhythmia therapy, using a therapy generation circuit in response to information about at least one of the arrhythmia status or an arrhythmia classification, such as information about one or more of the location or the type of the arrhythmia.

In Example 23, the subject matter of one or any combination of Examples 16-22 can optionally include instructions that, when executed by the processor, cause the IMD to inhibit generation of the arrhythmia therapy by the therapy generation circuit when the arrhythmia classification information indicates that an arrhythmia, such as an ongoing arrhythmia, is one or more of supraventricular in origin or hemodynamically stable.

Example 24 can include subject matter, or can be combined with the subject matter of one or any combination of Examples 1-23 (such as a system, a method, a means for performing acts, or a machine-readable medium including instructions that, when performed by the machine, cause the machine to perform acts, etc.) that can include a means of obtaining information indicative of a movement of an implantable lead via an electrical coupling of the lead to an IMD, where the movement can be due at least in part to a motion of a heart, a means of determining an arrhythmia status using the information indicative of the movement of the implantable lead, and a means of determining one or more of a location or a type of an arrhythmia, using the information indicative of the movement of the implantable lead, in response to the determined arrhythmia status indicating that an arrhythmia is occurring or has occurred.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
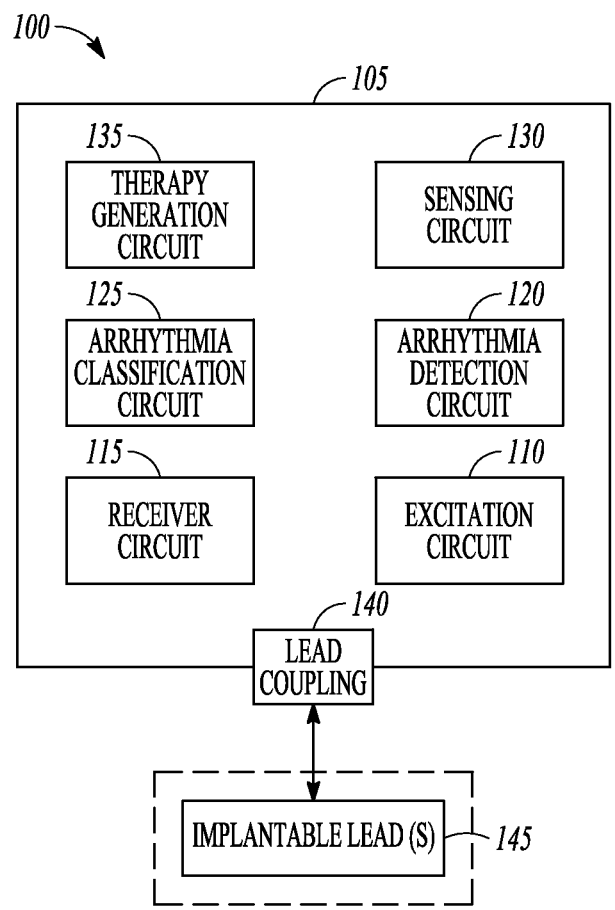
FIG. 1 illustrates generally an example of a portion of an ambulatory system for rhythm discrimination that can use information indicative of the movement of an implantable lead.

FIG. 1 illustrates generally an example of a portion of an ambulatory system 100 for rhythm discrimination that can use information indicative of the movement of an implantable lead. The ambulatory system 100 can include an ambulatory medical device, such as an implantable medical device (IMD) 105 that can include an excitation circuit 110, a receiver circuit 115, an arrhythmia detection circuit 120, an arrhythmia classification circuit 125, a sensing circuit 130, or a therapy generation circuit 135. In an example, the IMD 105 can include an interconnection, such as the lead coupling 140, configured to electrically couple the IMD 105 to one or more implantable leads, such as the implantable lead 145. One or more of the excitation circuit 110, a receiver circuit 115, an arrhythmia detection circuit 120, an arrhythmia classification circuit 125, a sensing circuit 130, or a therapy generation circuit 135 can be realized on or within a commonly shared substrate, such as on a commonly-shared integrated circuit, module, circuit board, or the like. In an example, one or more of the circuits of FIG. 1 can be included in one or more separate assemblies or separate ambulatory devices, such as using one or more wired or wireless communication techniques to exchange information between such devices.

The IMD 105 can include processing capability, such as a processor circuit. Various circuits, functions or other techniques described in the examples above and below can be implemented, such as using an application-specific integrated circuit (ASIC) configured to perform one or more particular functions, or a general-purpose circuit programmed to perform such functions. Such a general-purpose circuit can include a microprocessor, a microcontroller, or a programmable logic circuit, or a portion of one or more of these. In an example, the IMD can include a processor-readable medium such as a memory circuit (e.g., an EEPROM, an SRAM, or one or more other memory technology devices), and the processor circuit can be configured to perform one or more instructions stored on the processor-readable medium.

In an example, the IMD 105 can be configured to generate an electrostimulation, such as using one or more of a pacing or a cardiac resynchronization therapy (CRT) circuit (e.g., the therapy generation circuit 135). Such a therapy generation circuit 135 can be configured to generate bradycardia pacing or a resynchronization electrostimulation therapy for delivery to cardiac tissue, or one or more other therapies. In an example, the therapy generation circuit 135 can include a neural stimulator device, such as to provide electrical, mechanical, optical, acoustic or chemical stimulation to one or more neural targets.

In an example, the therapy generation circuit 135 can include one or more of: a pacing circuit, an anti-tachyarrhythmia therapy circuit, a cardiac resynchronization therapy circuit, a cardiac contractility modulation (CCM) circuit, or one or more other therapy generation circuits. For example, the anti-tachyarrhythmia therapy circuit can include a defibrillation circuit, or an anti-tachyarrhythmia pacing (ATP) circuit, or the like. In an example, the therapy generation circuit 135 can be configured to determine a therapy, or therapy protocol, such as to guide an arrhythmia therapy.

In an example, the therapy generation circuit 135 can be configured to withhold generation of a therapy when an arrhythmia condition is not present. In an example, the therapy generation circuit 135 can be configured to withhold, or delay, generation of an arrhythmia therapy, such as when a rhythm, such as a detected arrhythmia, has been determined to be supraventricular in origin.

In an example, the IMD 105 can include an excitation circuit, such as the excitation circuit 110 that can be coupled to at least one of the receiver circuit 115 or the implantable lead 145. The excitation circuit 110 can be configured to provide a time-varying signal including a first range of frequencies such as including a non-tissue stimulating, non-therapeutic electrical excitation signal, such as to one or more conductors comprising the implantable lead 145.

In an example, the excitation signal can include a time-varying voltage or current including one or more frequencies within a specified frequency range (e.g., a range from about 10 KHz to about 5 MHz, from about 5 MHz to about 30 MHz, from about 30 MHz to about 150 MHz, or including one or more other ranges of frequencies). In an example, the excitation signal can include a pulsed electrical signal, such as including one or more current or voltage pulses including a specified or desired amplitude, duration, pulse repetition rate, duty cycle, or morphology, among other parameters. In an example, the excitation circuit 110 can be coupled to one or more implantable leads, such as the implantable lead 145 via the lead coupling 140, such as using a header or other connector included as a portion, part, or component of the IMD 105.

In an example, an impedance measurement can be made at least in part using the excitation circuit 110, such as to obtain information indicative of lead motion. The impedance measurement can include injecting a current between a first terminal such as at least a portion of the lead coupling 140 and one or more other conductive elements, such as the housing of the IMD 105 or a second terminal, and measuring the voltage developed across the respective conductive elements. In an example, a synchronous current injection and voltage measurement can be used, such as discussed in relation to the physiologic impedance measurement techniques of the commonly assigned U.S. patent application Ser. No. 12/350,728, entitled "IMPEDANCE MEASUREMENT AND DEMODULATION USING IMPLANTABLE DEVICE," filed on Jan. 8, 2009, which is herein incorporated by reference in its entirety, including its description of injecting one or more non-tissue-stimulating bi-phasic current pulses and synchronously measuring the voltage induced by the one or more bi-phasic current pulses.

In an example, the implantable lead 145 can be coupled to circuitry within the IMD such as via the lead coupling 140 (e.g., a header or other connector block included as a portion of the IMD 105). For example, the implantable lead 145 can include one or more conductors (e.g., cardiac therapy delivery conductor, a cardiac electrical activity sensing conductor, etc.), such that can provide an electrical coupling between one or more electrodes located at or near tissue, such as cardiac tissue, and the IMD 105. In an example, the implantable lead 145 can be located at a site within or on the body (e.g., including one or more surface, subcutaneous, or intravascularly-located electrodes or conductors). In an example, the implantable lead 145 can be implanted or otherwise placed with a body, such as within or near a heart, such as for ambulatory monitoring, or therapy delivery, such as discussed in the examples of FIGS. 2-3.

In an example, the receiver circuit 115 can be electrically or communicatively coupled to one or more implantable leads, such as the implantable lead 145, such as through the lead coupling 140. In an example, one or more separate conductors in the implantable lead 145 can be attached to one or more terminal blocks such as included in a lead coupling 140 such as attached to a housing of the IMD 105. For example, the lead coupling 140 can provide electrical contact between the one or more conductors of the implantable lead 145 and circuitry within the IMD 105 (e.g., excitation circuit 110, the receiver circuit 115, the therapy generation circuit 135, etc.). In an example, the receiver circuit 115 can be configured to receive a response signal, such as including a signal indicative of the motion of the implantable lead, hereinafter referred to as a lead motion indicating (LMI) signal.

For example, a response signal can be received in response to an interaction between an excitation signal (e.g., provided by the excitation circuit 110) and the electrical characteristics of the implantable lead 145 (e.g., one or more motion-dependent passive electrical characteristics of the lead) such as during a movement of the implantable lead 145. For example, such electrical characteristics of the lead can vary as portions of the lead are compressed or flexed, such as altering the spacing between portions of one or more conductors included in the lead assembly. In an example, the receiver circuit 115 can be configured to receive or process one or more response signals received such as from the implantable lead 145 concurrently with or subsequently to the excitation circuit 110 providing the excitation signal to the one or more implantable leads.

In an example, the receiver circuit 115 can be configured to receive or process the response signal to determine an LMI signal. For example, the receiver circuit 115 can be configured to obtain information about the movement of a first implantable lead (e.g., a first LMI signal), such as located within, or near a first location of the heart using a first response signal received from the first implantable lead. The receiver circuit 115 can be configured to obtain information about the movement of a second implantable lead (e.g., a second LMI signal), such as located within or near a second location of the heart, using a second response signal received from the second implantable lead. For example, the information about the movement of an implantable lead can be a characteristic of the LMI signal (e.g., information about amplitude, frequency, phase, noise floor, signal-to-noise ratio, time interval between peaks, waveform shape, or one or more other characteristics).

In an example, the receiver circuit 115 can be configured to process the response signal (e.g., using a filter), such as to provide a time-varying signal indicative of the motion of the implantable lead (e.g., the LMI signal). For example, the response signal can include a first component (e.g., a carrier signal), such as including information about the excitation signal, and a second component (e.g., a signal indicative of lead motion that can modulate the carrier), such as the LMI signal. In an example, the LMI signal can include time-varying information indicative of the motion of the implantable lead. In an example, the receiver circuit 115 can be configured to provide the LMI signal, or a portion of the LMI signal to a circuit configured for signal processing (e.g., the arrhythmia detection circuit 120, the arrhythmia classification circuit 125, etc.) such as for one or more of detection or classification of an arrhythmia.

In an example, the receiver circuit 115 can be configured to determine amplitude information of one or more LMI signals. For example, the amplitude information can be determined such as by using one or more of a central tendency (e.g., an average, a median, a mean, etc.), a peak-to-peak determination, a peak determination, a root-mean-square determination, a statistical ranking (e.g., a percentile), or an absolute value of at least a portion of the LMI signal. In an example, the receiver circuit 115 can be configured to compare amplitude information such as can be obtained from the LMI signal to a criterion (e.g., a threshold) or to amplitude information of a second LMI signal from a second implantable lead. Such a comparison can be used to determine whether the LMI signal is to be sent to a signal processing circuit (e.g., the arrhythmia detection circuit 120, or the arrhythmia classification circuit 125) or otherwise triggers further analysis. Alternatively, if the amplitude information does not meet the criterion, the receiver circuit 115 can be configured to withhold transmission of the LMI signal, or otherwise indicate to the arrhythmia detection circuit 120, or the arrhythmia classification circuit 125 to withhold further analysis (e.g., when the amplitude of the response signal is below a threshold level indicating that extraction of motion information is not meaningful or is too noisy to meaningfully process).

In an example, the arrhythmia detection circuit 120 can be coupled to the receiver circuit 115, or the lead coupling 140. In an example, the arrhythmia detection circuit 120 can be configured to receive information, such as including the LMI signal, or other information derived from the LMI signal. For example, the arrhythmia detection circuit 120 can be configured to extract amplitude information from the LMI signal (e.g., a magnitude of at least a portion of the LMI signal within a specified frequency range).

Movement of the implantable lead 145 can include a physical displacement of one or more portions of the implantable lead 145, such as with respect to an equilibrium position. In an illustrative example, the implantable lead 145 can undergo a physical displacement, such as from a mechanical coupling to, or physical contact with, moving tissue. In an example, the information indicative of movement of the implantable lead 145 can include a time varying signal (e.g., a LMI signal), where the LMI signal corresponds to a movement of the heart (e.g., a cardiac contraction cycle, an impact of a heart valve to the implantable lead 145, a frictional contact of cardiac tissue to the implantable lead 145, or mechanical contact of the lead to vibrating tissue, etc.).

In an example, the arrhythmia detection circuit 120 can be configured to detect an arrhythmia using information (e.g., amplitude information) from the LMI signal such as within one or more frequency ranges. For example, the arrhythmia detection circuit 120 can be configured to compare amplitude information determined over a first frequency range to amplitude signal information determined over a second frequency range, such as from one or more LMI signals. In an example, the first frequency range can correspond to a lower frequency range (e.g., from about 0.05 to about 2 Hz), such that the obtained amplitude information can include information corresponding to movement of the myocardium, such as due to bending or compression of the implantable lead 145 during a normal cardiac contraction cycle. In an example, amplitude information such as determined over an upper frequency range (e.g., near 10 Hz) can correspond to motion indicative of an arrhythmia (e.g., ventricular arrhythmia, ventricular fibrillation, etc.). In an arrhythmic example, such as during an arrhythmia, the arrhythmia detection circuit 120 can obtain information including the second frequency range, such as due to motion associated with rapid or uncoordinated contractions of the heart (e.g., arrhythmia, fibrillation, etc.), even if gross myocardial motion is reduced or absent.

In an example, the arrhythmia detection circuit 120 can be configured to detect an arrhythmia such as by using amplitude information, such as a magnitude of the LMI signal within one or more specified frequency ranges. For example, the arrhythmia detection circuit 120 can be configured to compare an LMI signal magnitude to a criterion, such as comparing the magnitude of the LMI signal energy (e.g., a voltage, a current, a power, or a power-spectral estimate, etc.) within a specified frequency range, to a criterion. In an example, the arrhythmia detection circuit 120 can compare a relative indication of information (e.g., a difference, a ratio, etc.) of amplitude information of two or more LMI signal magnitudes to a threshold. For example, the arrhythmia detection circuit 120 can be configured to determine an arrhythmia by comparing a ratio of LMI signal magnitudes to a criterion. For example, the arrhythmia detection circuit 120 can be configured to compare a relative indication of information (e.g., a ratio, a difference, etc.) to a threshold, such as using an LMI signal magnitude within the upper frequency range as the numerator and an LMI signal magnitude within the lower frequency range as the denominator. An arrhythmia can be declared, for example, when the relative indication of information indicates that the portion of the energy in the LMI "spectrum" corresponding to the arrhythmic range of frequencies exceeds the portion of the energy in the LMI "spectrum" corresponding to a normal sinus rhythm.

In an example, the arrhythmia detection circuit 120 can be configured to declare an arrhythmia such by comparing a relative indication of information about LMI signal magnitudes determined during a first duration (e.g., an interval of time corresponding to current, possibly arrhythmic, cardiac activity) against LMI signal information obtained during a previous duration (e.g., a template of normal or arrhythmic activity). For example, the arrhythmia detection circuit 120 can be configured to determine a ratio of the LMI signal magnitude within the upper frequency range to a LMI signal magnitude within a lower frequency range within a current duration. The arrhythmia detection circuit 120 can be configured to compare the ratio of LMI signal magnitude information from the current duration to a ratio of LMI signal magnitude information from a previous duration such as using a criterion. For example, an arrhythmia can be declared when a comparison of the value of the ratio of the current duration to the value of the ratio of the previous duration meets the criterion, such as exceeding a threshold.

In an example, the IMD 105 can include the sensing circuit 130, such as to obtain a signal indicative of cardiac electrical activity. For example, the obtained signal can be used to provide a graphical representation of the cardiac electrical activity, such as an intracardiac electrogram. In an example, the IMD 105 can be configured to detect an arrhythmia condition, such as using signal information detected using the sensing circuit 130, such as magnitude or interval information from the signal representative of cardiac electrical activity, such as an electrogram. For example, the arrhythmia detection circuit 120 can be configured to use timing information, such as a time interval between successive atrial contractions, ventricular contractions, or both. In an example, the timing information can be compared to a criterion, such as to determine an indication of an arrhythmia when the criterion has been met (e.g., exceeding a threshold). In an example, the criterion can vary based on one or more physiological conditions, such as can be detected using the signal information (e.g., a magnitude or timing information of a signal indicative of cardiac electrical activity). For example, the criterion can vary using automatic gain control such as to modify a threshold following a sensed beat. In an example, the arrhythmia detection circuit 120 can be configured to use the LMI signal to confirm an arrhythmia condition diagnosis, such as to avoid delivering inappropriate therapy.

For example, the arrhythmia detection circuit 120 can be configured to confirm an arrhythmia condition diagnosis, such as an arrhythmia detected using an electrogram sensed by the sensing circuit 130. For example, the IMD 105 can be configured to detect an arrhythmia using interval information or one or more other criteria, such as using information about an electrical signal obtained by a sensing circuit 130.

For example, various systems and methods to detect an arrhythmia, such as a tachyarrhythmia, are described in the commonly assigned U.S. patent application Ser. No. 12/794, 346 entitled "Tachyarrhythmia Detection using Dynamic Duration," which is incorporated herein by reference in its entirety, including its description of using a heart rate or interval information to detect a tachyarrhythmia. In an example, the arrhythmia detection circuit 120 can be configured to use the LMI signal to confirm the arrhythmia diagnosis, such as using the arrhythmia condition detected by the sensing circuit 130. In an example, the arrhythmia detection circuit 120 can be configured to determine whether an arrhythmia is present using one or more of the LMI signal sensed before, concurrently, or after the sensing circuit 130 senses corresponding electrical cardiac activity indicative of an arrhythmia. For example, one or more of the LMI signal or the cardiac electrical activity can be sensed using one or more implantable leads. In an example, the arrhythmia detection circuit 120 can be configured to determine an arrhythmia status using one or more of morphology information or interval information, such as can be obtained from an LMI signal from one or more implantable leads. For example, the arrhythmia detection circuit 120 can determine interval information, such as an interval between successive peaks of the LMI signal magnitude. The arrhythmia detection circuit 120 can then be configured to determine an arrhythmia status such as by comparing the detected interval between successive peaks and a threshold, such that an arrhythmia can be declared when the threshold is exceeded. In an example, the arrhythmia detection circuit 120 can be configured to detect an arrhythmia condition, such as comparing an LMI signal morphology to a morphology template, such as a morphology of an LMI signal during a non-arrhythmia state. In an example, the arrhythmia detection circuit 120 can be configured to detect an arrhythmia condition, such as comparing an LMI signal morphology to at least a portion of a morphology template corresponding to an arrhythmia state. For example, the morphology template corresponding to an arrhythmia state (e.g., a stable sinus tachycardia arrhythmia) can be generated using an LMI signal associated with a high rate of atrial pacing (e.g., between about 140 and about 160 beats per minute) over a specified duration of time, such as generated using the therapy generation circuit 135.

In an example, the arrhythmia classification circuit 125 can be configured to be coupled to the arrhythmia detection circuit 120, or the receiver circuit 115 such as to discriminate between arrhythmia types using a mechanical contraction pattern of the heart. For example, the mechanical contraction pattern can be determined such as from an LMI signal, such as from the one or more implantable leads, such as the implantable lead 145. In an example, the mechanical contraction pattern can be used to discriminate between arrhythmia types, such as comparing at least a portion of the mechanical contraction pattern over a current duration to a portion of the mechanical contraction pattern from a previous duration, such as to use the previous mechanical contraction pattern as a template. In an example, arrhythmia classification circuit 125 can be configured use the LMI signal to detect a pattern of mechanical contractions of the cardiac muscle in response to an electrical depolarization. Such electrical depolarizations can originate in the atrial chambers such as to make use of the specialized conduction system in the heart (e.g., the SA node, the atrioventricular (AV) node, the bundle branches, etc.) to cause a characteristic mechanical contraction pattern. In an example, the mechanical contraction patterns can differ between individuals, such as due to a cardiac condition (e.g., prior myocardial infarction, a bundle branch block, etc.). In an example, such as during a supraventricular arrhythmia, one or more morphological features (e.g., the shape of a portion of the waveform) of the LMI signal can remain the same over time, however the time intervals or magnitude may vary due to physiological differences (e.g., filling times, rate-dependent conduction, shortened myocardial action potentials, etc.) over time. In an example, electrical or mechanical activity associated with a ventricular arrhythmia can be very different from supraventricular arrhythmias. In an example, a mechanical contraction pattern can be used to discriminate between ventricular and supraventricular arrhythmias, such as using LMI signal morphology or frequency components of the LMI signal such as due to the location or characteristics of the one or more implantable leads.

For example, the arrhythmia classification circuit 125 can be configured to determine, such as from an LMI signal, one or more of a location (e.g., atrium ventricle, etc.), or a type (e.g., ventricular, supraventricular, etc.) of an arrhythmia, such as in response to the arrhythmia detection circuit 120 determining that an arrhythmia is occurring or has occurred.

In an example, the arrhythmia classification circuit 125 can be configured to discriminate between arrhythmias such as by comparing an LMI signal obtained during a first duration of time (e.g., such as an LMI signal measured during an identified normal sinus rhythm, or an otherwise hemodynamically-stable rhythm) to an LMI signal obtained during second duration of time (e.g., during a time of an identified arrhythmia). In an example, the arrhythmia classification circuit 125 can be configured to determine an arrhythmia type, or arrhythmia location using one or more of (1) myocardial contraction morphology, (2) a myocardial contraction spectrum, or other techniques to analyze information corresponding to the motion of the implantable lead 145, such as including information obtained from an LMI signal.

For example, the arrhythmia classification circuit 125 can be configured to discriminate between arrhythmia types (e.g., a ventricular origin or locus, a supraventricular origin or locus, etc.), such as by analyzing an LMI signal using myocardial contraction morphology (e.g., using a technique similar to arrhythmia discrimination using a signal indicative of cardiac electrical activity). In an example, cardiac electrical activity can be examined using an electrical signal sensed using the sensing circuit 130 (e.g., examining an interval between cardiac electrical activity representative of ventricular or atrial contractions).

In an example, the IMD 105 can be configured to determine an arrhythmia classification using a morphology-based technique, such as disclosed in the commonly assigned U.S. Pat. No. 6,275,732, "Multiple Stage Morphology-Based System Detecting Ventricular Tachycardia and Supraventricular Tachycardia" which is incorporated herein by reference in its entirety, including its description of determining and classifying ventricular and supraventricular tachyarrhythmia using a signal representative of cardiac electrical activity.

The present inventors have recognized that an indication of cardiac electrical activity need not always correlate with mechanical cardiac contraction. For example, generally, an electromechanical delay can be present between detection of cardiac electrical activity a subsequent mechanical contraction. The sensed electrical signal alone may not reflect the delay between the time the heart receives the electrical signal and the time the cardiac muscle contracts. In an example, the arrhythmia classification circuit 125 can be configured to classify an arrhythmia using one or more of an LMI signal or a sensed signal representative of cardiac electrical activity, such as an electrogram obtained, for example, by the sensing circuit 130 via the implantable lead 145, or an external lead. In an example, the electrogram and the LMI signal can be obtained concurrently, such as using the same implantable lead 145. For example, the sensing circuit 130 can be configured to obtain a signal indicative of cardiac electrical activity such as before, during or after obtaining an LMI signal.

In an example, the arrhythmia classification circuit 125 can be configured to use a signal indicative of cardiac electrical activity (e.g., an electrogram) to provide a time reference such as to temporally align one or more features or regions of the obtained LMI signal to one or more features or regions of a cardiac activity signal or a cardiac event (e.g., an R-wave). In an example, arrhythmia classification circuit 125 can align a first time fiducial associated with an LMI signal corresponding to a first duration of time (e.g., during a sinus rhythm), to a second time fiducial associated with a second LMI signal corresponding to a second duration of time (e.g., during an arrhythmia). In an example, the arrhythmia classification circuit 125 can compare the first LMI signal to the second LMI signal to discriminate between arrhythmias or to determine an arrhythmia location. In an example, the comparison of the first LMI signal to the second LMI signal can be performed for each of the one or more implantable leads, such as the implantable lead 145.

In an example, the arrhythmia classification circuit 125 can be configured to determine a degree of similarity or correlation between the first LMI signal and the second LMI signal. In an example, the arrhythmia classification circuit 125 can be configured to compare LMI signal information indicative of a normal sinus rhythm to LMI signal information associated with a duration of an unknown (e.g., possibly arrhythmic) LMI signal. For example, the information indicative of a normal sinus rhythm can be compared to the information of the unknown LMI signal such as by using a threshold (e.g., a difference exceeds the threshold).

In an example, the arrhythmia classification circuit 125 can be configured to determine whether the first LMI signal is the same as, or different from the second LMI signal, such as by correlating the first LMI signal and the second LMI signal and comparing a correlation value to a criterion. For example, the first LMI signal can be deemed different than the second LMI signal if the correlation value is less than the criterion. In an example, the arrhythmia classification circuit 125 can be configured to determine whether the first LMI signal is the same as or different from the second LMI signal for each of the one or more implantable leads, such as the implantable lead 145.

In an example, the arrhythmia classification circuit 125 can be configured to determine whether the arrhythmia has a ventricular or supraventricular origin using the determinations of whether the first LMI signal is the same as or different from the second LMI signal for the one or more implantable leads, such as the implantable lead 145. In an example, the arrhythmia classification circuit can classify a ventricular arrhythmia as a result of a supraventricular determination. For example, if the arrhythmia classification circuit 125 determines that a detected arrhythmia is not supraventricular, then the arrhythmia classification circuit 125 can deem the arrhythmia to have ventricular origin. For example, the arrhythmia detection circuit 125 can identify a supraventricular arrhythmia, such as by determining a 1:1 correlation exists between atrial and ventricular beats. In an example, a ventricular arrhythmia can be identified, such as by using the LMI signal, when an indication of an atrial beat, if even present, is followed by indications of two or more ventricular beats.

In an example, an arrhythmia can be classified using information about a location of high-rate or uncoordinated activity, such as using one or more LMI signals received from the one or more implantable leads. In an example, the arrhythmia classification circuit 125 can be configured to determine whether a detected arrhythmia has ventricular or supraventricular origin, such as by comparing the arrhythmia indications determined from the one or more LMI signals to a criterion. For example, the criterion can be determined using a LMI signal during a duration of a known sinus rhythm of the subject's heart such as a 1:1 correlation of atrial beats to ventricular beats within a specified heart rate (e.g., sixty to one hundred beats per minute). In an example, the arrhythmia classification circuit 125 can be configured to determine a ventricular or supraventricular determination from the LMI signal information, such as by using timing information or morphology information obtained during a duration. For example, a ventricular arrhythmia can be indicated, such as when a count of indicated ventricular beats exceeds a count of identified atrial beats during a specified duration. Similarly, if an identified ventricular contraction follows an atrial contraction, during a duration, the arrhythmia can be determined to be supraventricular. For example, if the one or more LMI signals indicative of a supraventricular arrhythmia meet a criterion, such as exceed a threshold, the arrhythmia can be deemed supraventricular.

In an example, the arrhythmia classification circuit 125 can be configured to combine two or more LMI signals, received from the one or more implantable leads by the receiver circuit 115, into a composite LMI signal. For example, the LMI signal can be combined, such as using a mixer circuit, such as to provide a composite signal including phase, magnitude, or frequency information of the combined signals (e.g., a signal proportional to the sum of the one or more LMI signals). In an example, a first composite LMI signal, such as corresponding to a duration of a sinus or otherwise supraventricular rhythm, can be determined by the arrhythmia classification circuit 125 and stored in memory. In an example, the arrhythmia classification circuit 125 can be configured to compare the first composite LMI signal to a second composite LMI signal, such as corresponding to a duration of an identified arrhythmia, such as to determine whether the first composite LMI signal is similar to, or different from the second composite LMI signal.

In an example, the arrhythmia classification circuit 125 can be configured to determine a correlation value, such as resulting from a multi-dimensional correlation, using the first composite LMI signal and the second composite LMI signal to determine whether the second composite LMI signal has a supraventricular origin. For example, the arrhythmia classification circuit 125 can be configured to compare the determined correlation value to a criterion (e.g., a threshold), such as to determine that the second composite LMI signal corresponds to a supraventricular arrhythmia when the correlation value is greater than the criterion.

In an example, the arrhythmia classification circuit 125 can be configured to use one or more criteria, such as to determine whether an arrhythmia has a ventricular or supraventricular origin. In an example, each of the one or more criteria can be the same as or different than another criterion. In an example, the one or more criteria can use a specified value (e.g., a fixed specified threshold value, a specified threshold value capable of being programmed by a user, etc.), or can be a function of one or more signals (e.g., a physiological signal from the sensing circuit 130, an LMI signal received by the receiver circuit 115, etc.) such as received by the IMD 105. For example, a criterion can be determined using an LMI signal received from the implantable leads 145, such as during a duration corresponding to a normal sinus rhythm. In an example, the criterion can vary as a function of one or more features of the LMI signal. For example, the criterion can correspond to a one to one correlation of atrial beats and ventricular beats. In an example, the criterion can correspond to a time interval, such as a time interval between atrial events, ventricular events or between an atrial and a ventricular event.

In an example, the arrhythmia classification circuit 125 can be configured to discriminate between type, and location of an arrhythmia, such as between a supraventricular arrhythmia, and a ventricular arrhythmia using a myocardial contraction spectrum. In an example, the myocardial contraction spectrum can include frequency component information from one or more frequency ranges associated with one or more LMI signals.

For example, the arrhythmia classification circuit 125 can be configured to identify an arrhythmia or classify an identified arrhythmia such as by using magnitude information associated with each of the one or more frequency ranges of an LMI signal. For example, the magnitude information can be used to determine whether an arrhythmia has a ventricular or supraventricular origin. In an example, the magnitude information from the one or more frequency components of the one or more LMI signals can be compared to one or more criteria (e.g., a threshold), such that the arrhythmia classification circuit can identify an arrhythmia or discriminate between a supraventricular arrhythmia and a ventricular arrhythmia. For example, the arrhythmia detection circuit 125 can be configured to determine whether an arrhythmia has supraventricular, or ventricular origin using a comparison of a relative indication of information (e.g., an unsigned difference, a ratio, etc.) between the magnitude and a criterion. For example, arrhythmia detection circuit 125 can determine that an arrhythmia has ventricular origin over a frequency range such as when the unsigned difference between the magnitude information and the criterion satisfies a threshold. For example, an LMI signal can be determined to correspond to an arrhythmia, such as a ventricular arrhythmia, over a frequency range when the value of the unsigned difference between the magnitude information of the LMI signal and the criterion satisfies a threshold.

In an example, the arrhythmia detection circuit 120 or the arrhythmia classification circuit 125 can be configured to determine an arrhythmia condition using one or more frequency components of one or more LMI signals. For example, the arrhythmia can be determined to be a supraventricular arrhythmia when one or more frequency ranges determined to have supraventricular origin satisfies a criterion (e.g., exceeds a threshold). In an example, the arrhythmia can be determined to be ventricular when the number of the one or more frequency ranges determined to have ventricular origin satisfies a criterion.

For example, a criterion associated with a first frequency range, (e.g., about 0.05 Hz to about 2 Hz) can correspond to LMI signal information indicative of movement of the implantable lead 145 (e.g., bending, compression, flexing, etc.) due to normal myocardial contractions such as corresponding to a sinus rhythm. In an example, the criterion associated with a second frequency range (e.g. above about 2 Hz to near 10 Hz) can correspond to movement of the implantable lead 145 due to rapid or uncoordinated motion of the myocardium, such as due to a re-entrant arrhythmia or fibrillation.

Figure 2:
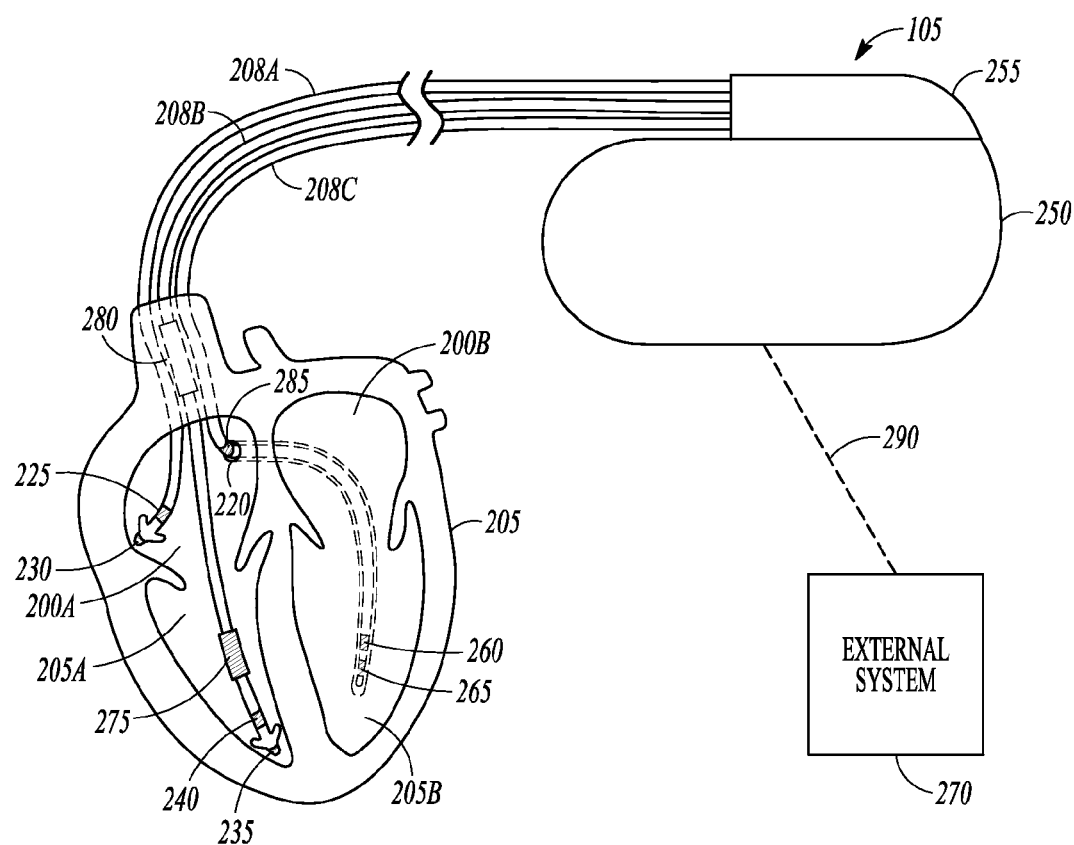
FIG. 2 illustrates generally a portion of a system that can include an implantable medical device.

FIG. 2 illustrates generally a portion of a system that can include an IMD 105. Examples of the IMD 105 can include cardiac function management (CFM) devices such as including one or more of implantable pacemakers, implantable cardioverter-defibrillators (ICDs), cardiac resynchronization therapy devices (CRTs), or one or more other devices. The system can include an IMD programmer or other external device 270, such as a local monitoring device, capable of communicating wirelessly, such as via wireless communication using a communicative coupling 290 with the IMD 105, using a communication or computer network, radio frequency (RF) signals, or other telemetry capabilities. In an example, a remote monitoring device can be communicatively coupled, such as via a communication or computer network, to a remote monitoring device, such as at a location different from the local monitoring device (e.g., a central server, a remotely-located caregiver workstation, etc.).

The IMD 105 can be coupled via one or more leads 208A-C to the heart 205. Cardiac leads 208A-C (e.g., implantable lead 145) can include a proximal end coupled to the IMD 105 and a distal end, capable of being electrically coupled by one or more electrodes to one or more portions of the heart 205. The electrodes can deliver cardioversion, defibrillation, pacing, or resynchronization therapy, or combinations thereof, such as from the therapy generation circuit 135, to one or more chamber of the heart 205. The electrodes can be electrically coupled to sense amplifiers configured to receive electrical signals indicative of cardiac activity, such as the sensing circuit 130.

The heart 205 includes a right atrium 200A, a left atrium 200B, a right ventricle 205A, a left ventricle 205B, and a coronary sinus 220 extending from right atrium 200A. The atrial lead 208A can include electrodes (e.g., electrical contacts, such as a ring electrode 225, and a tip electrode 230, etc.) capable of being disposed in the atrium 100A of the heart 205, such as for sensing signals, delivering pacing therapy, or both, to the atrium 200A.

The right ventricular lead 208B can include one or more electrodes, such as the tip electrode 235 and the ring electrode 240, such as for sensing signals, delivering pacing therapy, or both. The lead 208B can also include additional electrodes, such as for delivering atrial cardioversion, atrial defibrillation, ventricular cardioversion, ventricular defibrillation, or combinations thereof to the heart 205. Such electrodes can have larger surface areas than do pacing electrodes, such as to handle larger energies involved in defibrillation. In an example, the lead 208B can deliver resynchronization therapy to the heart 205.

The IMD 105 can include a third cardiac lead 208C capable of being attached to the IMD 105 through the header 255. The third cardiac lead 208C can include one or more electrodes such as electrodes 260 and 265, such as placed in a coronary vein nearby the left ventricle (LV) 205B. The third cardiac lead 208C can include a ring electrode 285, such as positioned near the coronary sinus (CS) 220.

The lead 208B can include one or more of a first defibrillation coil electrode 275, such as located proximal to the tip and ring electrodes 235, 240, such as for placement in a right ventricle (RV), or a second defibrillation coil electrode 280, such as located proximal to the first defibrillation coil 275, the tip electrode 235, and the ring electrode 240, such as for placement in or near the superior vena cava (SVC). In an example, a cardioversion or a shock therapy can be delivered from the first coil (e.g., the RV coil 275) to the second coil (e.g., the SVC coil 280). In an example, the SVC coil 280 can be electrically tied to an electrode formed on a hermetically-sealed IMD housing 250 ("can"), such as to provide an adjustable defibrillation "vector" or "pathway" for energy to pass between the RV coil 275 and the housing 250 via the myocardium. In an example, the therapy can be delivered from the RV coil 275, such as only to the electrode formed on the IMD can 250. The present methods and systems can be adjustably configured to provide one or more pacing or defibrillation therapies across specified electrode configurations, such as using information about electrical or mechanical cardiac activity as described in the examples above and below.

Figure 3:
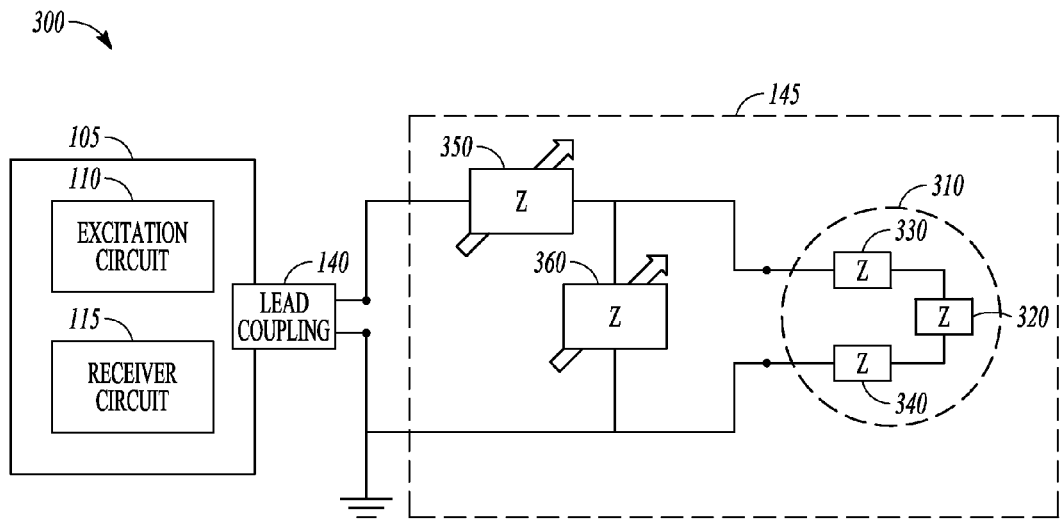
FIG. 3 illustrates generally a portion of a system that can include detecting information indicative of the movement of the implantable lead.

FIG. 3 illustrates generally a portion of a system 300 that can include detecting information indicative of the movement of one or more implantable leads, such as the implantable lead 145. In an example, the system 300 can include an IMD 105, and the implantable lead 145, such as configured to provide a therapy (e.g., an arrhythmia therapy) to a heart 205, to sense a physiological signal associated with a subject (e.g., an electrogram) or both. In an example, the IMD 105 can include the excitation circuit 110 and the receiver circuit 115, and the lead coupling 140 as described above. In an example, the implantable lead 145 can be configured to be implanted within a subject such that a distal end of the lead body 310 can be located within or near the heart 205 (e.g., at a tissue interface location), and a proximal end can be configured to be electrically coupled to the IMD 105 (e.g., at the lead coupling 140), such as to provide a therapy, to sense a physiological signal, or both. In an example, the excitation circuit 110 can be configured to provide an excitation signal to the implantable lead 145. In an example, an interaction of the excitation signal and the electrical characteristics of the implantable lead can provide a response signal, such as can be received by the receiver circuit 115.

In an example, the implantable lead 145 can include one or more conductors (e.g., filers), such as one or more filers that spiral or otherwise traverse the length of the lead, such as from a connector at the proximal end of the lead to one or more electrodes along the lead or near the distal end. In an example, a lead body can be represented as a combination of resistive, capacitive, and inductive elements. In an example, the electrical characteristics of the implantable lead can be represented, such as using lead body impedance (e.g., a lead impedance 350-360) and the distal end of the lead can be modeled, such as using one or more of an electrode impedance 330-340, a cardiac tissue interface impedance 320, or the like. In an example, the impedance 330-360 can represent the electrical characteristics of various lead portions (e.g., passive electrical characteristics such as the resistance of a filer, an inductance of a loop formed by one or more filers, a capacitance between one or more filers, etc.) over a specified frequency range. In an example, the tissue interface impedance can include an electrode impedance, such as a characteristic impedance of an electrode, and an impedance 320 at the tissue interface impedance, such as an impedance corresponding to a connection of the implantable lead to the cardiac tissue.

In an example, the impedances 320-360 can vary over a specified frequency range (e.g., from about 10 KHz to about 100 KHz, from about 5 MHz to about 30 MHz, from about 30 MHz to about 150 MHz, etc.) corresponding to one or more of capacitive or inductive coupling between two or more portions of the implantable lead 145. In an example, an implantable lead can include an active element, such as an accelerometer, or piezoelectric elements, that can be used to obtain information about the motion of the implantable lead separately from, or additionally to the passive electric characteristics.

Figure 6:
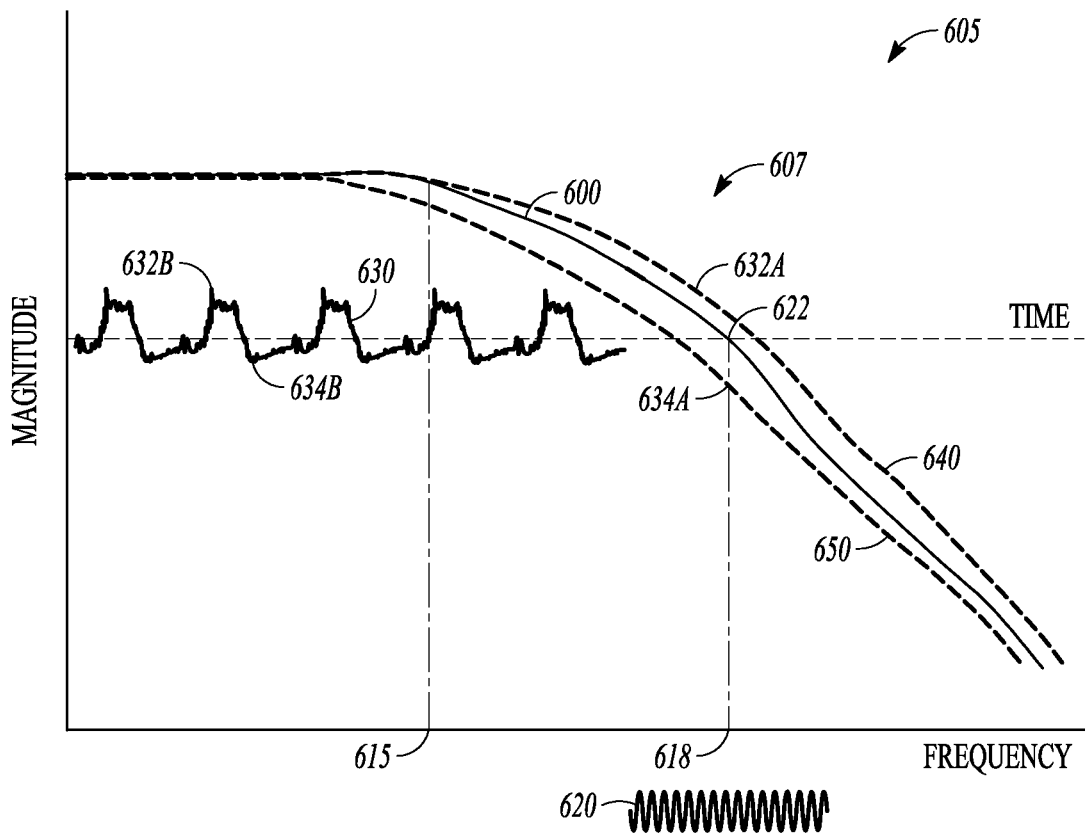
FIG. 6 illustrates generally an illustrative example of a relationship between the magnitude of a response signal versus frequency.

In an example, the electrical characteristics of the implantable lead can vary as a function of frequency, such as shown in FIG. 6, over a specified frequency range, such as a result of the capacitive or inductive interaction between a conductive portion of the lead and another conductor located within either the lead or elsewhere. In an example, the implantable lead 145 can be physically connected to the heart 205, or physically located near or within the heart 205, such that movement of the heart (e.g., a cardiac contraction cycle) can result in movement of the lead body. In an example, the movement of the lead body can cause a corresponding change to the electrical characteristics (e.g., lead capacitance, lead inductance, etc.).

For example, the lead impedances 350-360 can vary as a function of time corresponding to the movement of the implantable lead, such as during a cardiac cycle. Lead motion can include movement, or physical manipulation, of the implantable lead due to motion, such as caused by a cardiac contraction cycle (e.g., bending, stretching, twisting, impact, torsion, compression, etc.). In an example, the motion of the implantable lead 145 can include physical disturbance to the lead due to impacts, (e.g., a heart valve impact), frictional movement (e.g., frictional contact to cardiac tissue, or other tissue), radial compression (e.g., such as due to variation in blood pressure), or the like. In an example, lead motion can include, physical translation, or rotation of the lead body relative to a point fixed in space (e.g., a point on the body, inertial frame, etc.), such as might be measurable with a lead based accelerometer.

Figure 4:
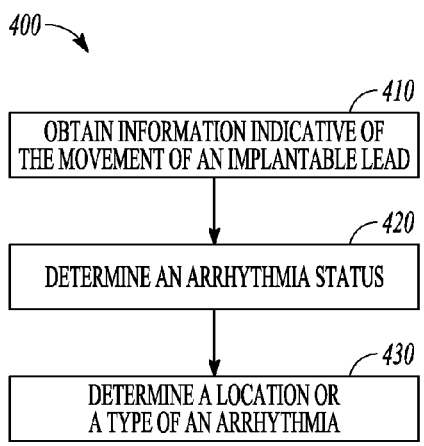
FIG. 4 illustrates generally an example of a technique for rhythm discrimination that can include using information indicative of the movement of the implantable lead.

FIG. 4 illustrates generally an example of a technique for rhythm discrimination that can include using information indicative of the movement of the implantable lead. At 410, information indicative of the motion of the implantable lead 145 can be obtained, such as using a response signal received from the implantable lead 145. In an example, the receiver circuit 115 can be configured to receive a response signal, such as received from the implantable lead 145, in response to a an excitation signal, such as delivered by the excitation circuit 110. In an example, the excitation circuit 110 can deliver an excitation signal over a specified frequency range. In an example, the interaction of electrical characteristics of the implantable lead 145 and the excitation signal can generate the response signal. In an example, the electrical characteristics of the implantable lead 145, such as the lead impedances 350-360, can change, such as in response to a motion of the implantable lead, such as caused by a motion of the heart 205. For example, the lead impedances 350-360, such as due to capacitive, or inductive coupling, can vary in time, such as caused by the time-varying motion of the implantable lead 145. In an example, a time-varying response signal, such as an LMI signal received by the receiver circuit 115 of the IMD 105, can be received in response to the interaction of the time-varying electrical characteristics and the excitation signal.

At 420, an ambulatory device, such as the IMD 105, can be configured to determine an arrhythmia status, such as by using the arrhythmia detection circuit 120 to determine whether an arrhythmia is occurring or has occurred. For example, the arrhythmia detection circuit can be configured to determine whether an arrhythmia condition is occurring or has occurred, such as by analyzing the LMI signal received from the implantable lead 145.

In an example, the arrhythmia detection circuit 120 can be configured to obtain information, such as a magnitude of energy or voltage corresponding to a corresponding to two or more frequency ranges included in the LMI signal. The frequency ranges can include a first frequency range generally indicative of a normal cardiac contraction cycle (e.g., about near-DC to about 2 Hz), or a second frequency range indicative of an arrhythmia (e.g., above about 2 Hz to near 10 Hz). In an example, LMI signal information can be analyzed, such as by comparing the information from the LMI signal to a criterion, (e.g., comparing a magnitude at a first frequency range to a criterion, comparing a magnitude at a second frequency range to a criterion), to detect whether an arrhythmia condition is occurring, or has occurred. For example, the arrhythmia detection circuit 120 can compare a relative indication of information of LMI signal magnitudes to a threshold, such as a relative indication of information of the LMI signal magnitude over the second frequency range to the LMI signal magnitude over the first frequency range. In an example, an arrhythmia can be declared if the relative indication of information of the LMI signal magnitudes is greater than the threshold.

In an example, the arrhythmia detection circuit 120 can analyze an LMI signal, such as to confirm a detected arrhythmia condition detected using a signal, such as representative of cardiac electrical activity, received from the sensing circuit 130. In an example, the arrhythmia detection circuit 120 can be configured to determine whether an arrhythmia is present, such as using an LMI signal, concurrently with the sensing circuit 130 determining whether an arrhythmia condition is present.

At 430, an ambulatory device, such as the IMD 105, can be configured to determine a location, or type of an arrhythmia (e.g., arrhythmia classification), such as by using the arrhythmia classification circuit 125. In an example, the arrhythmia classification circuit 125 can be configured to determine an arrhythmia classification after a determination of whether an arrhythmia condition is present, such as an arrhythmia detected using at least one of the sensing circuit 130, or the arrhythmia detection circuit 120. In an example, the arrhythmia classification circuit 125 can be configured to classify a detected arrhythmia condition as having ventricular or supraventricular origin. For example, the arrhythmia classification circuit 125 can be configured to classify an arrhythmia condition using (1) myocardial contraction morphology, or (2) a myocardial contraction spectrum as described above.

Figure 5:
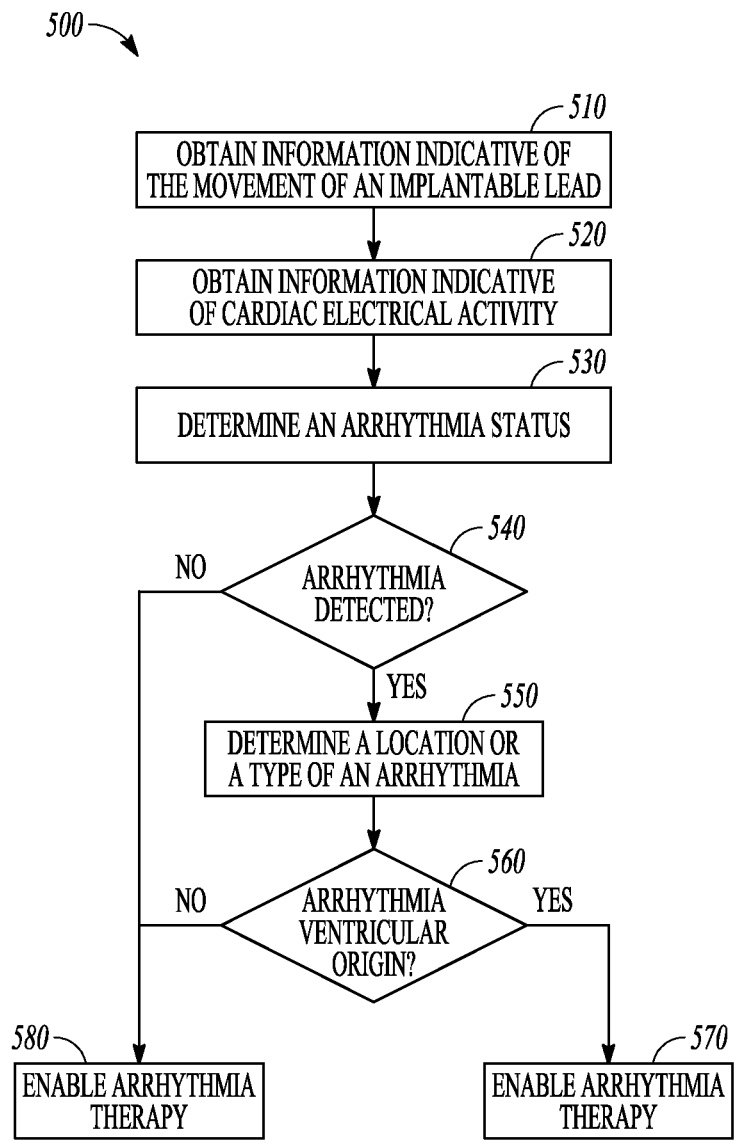
FIG. 5 illustrates generally an example of a technique that can include using rhythm discrimination to guide an arrhythmia therapy.

FIG. 5 illustrates generally an example of a technique that can include guiding arrhythmia therapy, such as a therapy generated via the therapy generation circuit 135. At 510, information indicative of the motion of an implantable lead, such as an LMI signal, can be obtained via the implantable lead 145 located within or near the heart 205. For example, the interaction of the electrical characteristics of the implantable lead 145 and the excitation signal generated by the excitation circuit 110 can provide the LMI signal. In an example, the motion of the implantable lead can cause variation in the electrical characteristics of the implantable lead due to capacitive or inductive couplings between two or more conductors, such as a conductor included in the implantable lead and a second conductor (e.g., a conductive housing of the IMD or an "indifferent" electrode located near the housing of the IMD). In an example, a time-varying motion, such as a cardiac contraction cycle, can cause the electrical characteristic to vary with respect to time.

At 520, a signal indicative of cardiac electrical activity can be received by the IMD 105, such as using the sensing circuit 130, from the implantable lead 145. In an example, the sensing circuit 130 can receive the signal indicative of cardiac electrical activity from the implantable lead 145 before, during, or after the LMI signal. For example, the sensing circuit 130 can be configured to receive a signal from which interval information can be obtained, such as between successive electrical depolarizations, such as to sense an arrhythmia condition according to one or more rate-based or interval-based criteria.

At 530, an arrhythmia status can be determined, such as from an LMI signal, or a signal indicative of cardiac electrical activity, or both. In an example, the LMI signal can be analyzed, such as by the arrhythmia detection circuit 120, to determine whether an arrhythmia is occurring or has occurred. For example, the arrhythmia detection circuit 120 can be configured to analyze a magnitude of the LMI signal over one or more frequency ranges, such as to compare the magnitude of the LMI signal to a criterion, such as a threshold, to determine whether the LMI signal is indicative of an arrhythmia. In an example, the arrhythmia detection circuit 120 can be configured to analyze the LMI signal, such as to confirm an arrhythmia determination, such as an arrhythmia determination made using a heart rate indicating signal by the sensing circuit 130. In an example, an arrhythmia status can be determined via interval information, such as between successive mechanical contractions as indicated in the LMI signal in the time-domain.

At 540, if an arrhythmia was detected, such as by the arrhythmia detection circuit 120, the IMD 105 can determine an arrhythmia classification, such as to classify the arrhythmia as ventricular or supraventricular, at 550. However, if an arrhythmia condition was not detected, then the IMD 105 can inhibit an arrhythmia therapy, such as at 580.

At 550, the location, or a type of an arrhythmia, such as detected at 530, can be determined, such as using the arrhythmia classification circuit 125. In an example, the arrhythmia classification circuit 125 can be configured, such as to determine whether the detected arrhythmia has a ventricular or supraventricular origin. For example, the arrhythmia classification circuit 125 can be configured to use myocardial contraction morphology, or a myocardial contraction spectrum to determine whether an LMI signal is indicative of a supraventricular, or ventricular arrhythmia, such as described above.

At 560, the ICD 105 can determine whether to enable or inhibit a therapy, such as an arrhythmia therapy delivered to the heart 205 for treatment of the detected arrhythmia. In an example, the determination of the location, or type of arrhythmia, such as a ventricular or supraventricular arrhythmia classification, can be used to determine whether to enable or inhibit an arrhythmia therapy. For example, if, at 560, the detected arrhythmia is determined to be supraventricular in origin, or otherwise hemodynamically-stable, an anti-tachyarrhythmia pacing (ATP) therapy can be generated before or instead of attempting a shock therapy. However, if, at 560, the arrhythmia is determined to be ventricular, or otherwise life-threatening, a shock arrhythmia therapy can be enabled at 570, such as for generation by the therapy generation circuit.

FIG. 6 illustrates generally an illustrative example of a relationship between the magnitude of a response signal versus frequency. As described above, the IMD 105 can include a receiver circuit 115, for example, configured to receive a signal indicative of the motion of the implantable lead, such as the response signal, received in response to an excitation signal provided by the excitation circuit 110. In an example, the magnitude 600 of the response signal can vary as a function of frequency due the electrical characteristics of the implantable lead 145 over a specified frequency range. For example, a relatively stable or "flat" magnitude response (e.g., a magnitude value within a defined range) can result from the interaction of the electrical characteristics of the implantable lead 145 and the excitation signal in a first frequency range 605, such as between DC or near-DC (e.g., about 0 Hz) and a second frequency 615 (e.g., about 10 KHz), such as due to the resistive components of the lead impedances 350-360 having more influence than the capacitive, or inductive components. However, for an excitation signal within a second frequency range 607 (e.g., from about 10 KHz to about 150 MHz), the capacitive or inductive elements of the lead impedances 350-360 can dominate the response, such as causing the response signal magnitude 610 to decline as a function of frequency over the second frequency range 607.

In an example, the interaction of an excitation signal at a frequency, such as frequency 617, and the electrical characteristics of the implantable lead 145 can result in a response signal 620, such as having a magnitude 622. In an example, the electrical characteristics of the implantable lead 145 can result from inductive or capacitive coupling between portions of the implantable lead such as due to the position and or location of the implantable lead 145 within or near the heart. In an example, the motion of the heart, such as a cardiac contraction cycle, can result in corresponding motion of the implantable lead 145. In an example, the motion of the implantable lead can cause the electrical characteristics of the implantable lead 145 to vary as a function of time. For example, the motion of the implantable lead can cause the magnitude of the response signal to vary as a function of time over a specified frequency range, such as the magnitude signals 640, 650, such as resulting from the variance in the electrical characteristics due to motion of the implantable lead caused, at least in part, by motion of the heart 205.

In an example, an excitation signal at a frequency 617, such as provided by the excitation circuit 110, can interact with the time-varying electrical characteristics of the implantable lead 145, such as to provide a signal indicative of the motion of the implantable lead (e.g., a response signal at least in part including an LMI signal 630). For example, the excitation signal at a frequency 617 can interact with the time-varying electrical characteristics of the implantable lead 145 during motion of the implantable lead. The motion of the implantable lead 145, such as caused a cardiac contraction cycle, can result in a response signal at a specified frequency having a time-varying magnitude value that can vary between a peak value 632A and a minimum value 634A. In an example, the response signal can include a carrier signal at the excitation frequency 617, and a modulating signal, such as a time-varying component resulting from the motion of the implantable lead (e.g., the LMI signal 630). For example, the magnitude of the LMI signal 630 can correspond to the time-varying magnitude of the response signal at the specified frequency such that the magnitude of the LMI signal 630 can vary between a peak value 632B and a minimum value 634B. In an example, the response signal can be conditioned such as to extract or otherwise provide the LMI signal for use by an analysis circuit, such as the arrhythmia classification circuit 120. Phase information can also be obtained, such as with respect to a reference phase corresponding to the excitation signal. Thus, the techniques above can be applied generally to magnitude or phase information, or to a real part or imaginary part of the response signal, in the case of a complex response signal.

Figure 7:
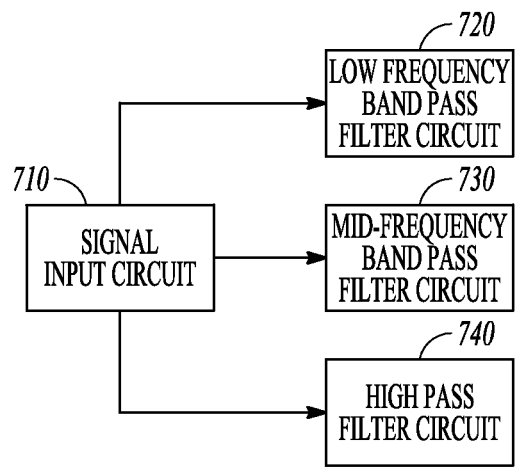
FIG. 7 illustrates generally an example of a system that can be used for conditioning a signal.

FIG. 7 illustrates generally an example of a system that can be used for conditioning a response signal for analysis. In an example, the receiver circuit 115 can include a signal input circuit 710, such as configured to receive a response signal from the implantable lead 145. In an example, the signal input circuit 710 can include circuitry such as configured to provide the LMI signal such extracted or otherwise obtained from the response signal. For example, the LMI signal can be obtained via demodulation, such as to remove a carrier frequency 617, such as to provide the LMI signal (e.g., via AM demodulation such as envelope detection or filtering, or via FM demodulation such as using a phase-locked loop, etc.). In an example, the LMI signal can include information about the motion of the implantable lead, such as caused by mechanical manipulation of the one or more leads caused by motion of at least one of the heart muscle, a heart valve, respiratory musculature, lungs, skeletal musculature, a variation in blood pressure, or other forces acting directly on the one or more leads.

In an example, the receiver circuit 115 can include one or more filters to provide information about one or more physiological conditions associated with the heart, such as information about the motion of the implantable lead in the LMI signal. In an example, the implantable lead 145 can be moved slowly, such as due to bending resulting from a cardiac contraction cycle. The implantable lead 145 can move quickly, such as caused by an impact on the lead resulting from a valve closure. In an example, the LMI signal can be filtered in one or more frequency ranges, such as to distinguish between one or more causes of the motion of the implantable lead. In an example, the receiver circuit 115 can include a low-frequency band pass filter circuit 720, a mid-frequency band pass filter circuit 730, or a high pass filter circuit 740. In an example, the filter circuits 720-740 can include a near-DC filter circuit, such as a high pass filter circuit configured to attenuate or remove signal noise under a frequency (e.g., about 0.05 Hz), configured to provide a baseline such as by filtering near-DC signal components. For example, the baseline can correspond to a near zero-energy or near-zero magnitude LMI signal when the implantable lead is not moving. In an example, the near-DC filter circuit can be included in one or more of the low-frequency band pass filter circuit 720, the mid-frequency band pass filter circuit 730, or the high pass filter circuit 740.

In an example, the low-frequency band pass filter circuit 720 can be configured to filter the LMI signal, for example, at a low frequency range (e.g., from about 0.05 Hz to about 10 Hz), such as to provide information indicative of the motion of the implantable lead 145, such as due to mechanical motion of the heart 205. For example, the low-frequency band pass 720 filter can provide a filtered LMI signal representative of the motion of the implantable lead due to motion caused by a cardiac contraction cycle. In an example, the filtered LMI signal can provide information representative of motion of the one or more implantable leads such as can be useful for verification of capture of a pacing pulse, managing fusion in capture detection applications or CRT applications, or monitoring to detect a lead dislodgment. In an example, the filtered LMI signal can be used for monitoring myocardial contraction such as to optimize a CRT therapy, to detect myocardial ischemia, to determine relative changes in stroke volume, or cardiac output, to detect abnormalities with relaxation of the cardiac muscle, or to detect abnormal mechanical contraction and to monitor electro-mechanical delay in the myocardium.

In an example, the mid-frequency band pass filter circuit 730 can be configured to filter the LMI signal, such as over a mid-frequency range (e.g., from about 0.05 Hz to about 30 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by a cardiac contraction cycle. For example, the filtered LMI signal can provide information useful for decompensation detection, rhythm discrimination using myocardial contraction morphology or myocardial contraction spectrum, to guide therapy to determine if ATP should be attempted before a shock, or to determine the timing of the shock, arrhythmia detection, or assessing autonomic function. In an example, the filtered LMI signal can be used to monitor the integrity of the implantable lead.

In an example, the high pass filter circuit 740 can be configured to filter the LMI signal, such as to filter signal out signal components under a specified frequency range (e.g., above about 10 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by one or more portions of the heart during a cardiac contraction cycle (e.g., a valve impact, frictional contact between cardiac muscle and the implantable lead, etc.). For example, the filtered LMI signal can provide information useful to detect heart sounds, or to detect the timing and amplitude of valve impact on leads. In an example, the filtered LMI signal can be used to detect lead maturity (e.g., a connection between myocardial tissue and the implantable lead 145), or lead dislodgement. In an example, the filtered LMI signal can be used for dissynchrony measurement or CRT optimization, such as by detecting right side and left side heart sounds.

Figure 8:
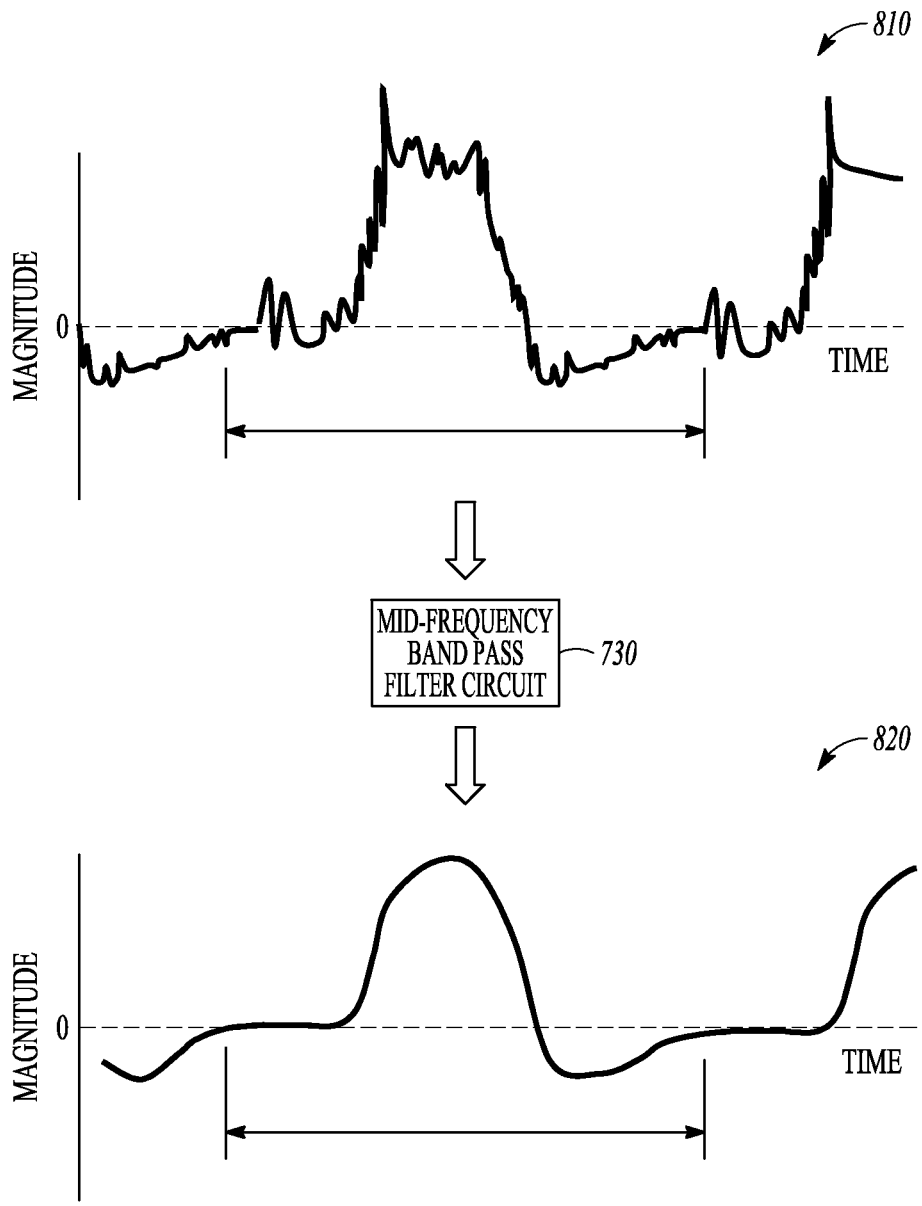
FIG. 8 illustrates generally an illustrative example that can include filtering or otherwise conditioning a response signal.

FIG. 8 illustrates generally an illustrative example that can include filtering or otherwise conditioning a response signal. In an example, an LMI signal can be received by the receiver circuit 115, such as can include an LMI signal indicative of the motion of the implantable lead 145, such as the LMI signal 810. In an example, the LMI signal 810 can be filtered, such as to provide information about the cardiac contraction cycle. For example, the LMI signal 810 can be filtered, such as by the mid-frequency band pass filter 730, such as to provide a filtered LMI signal 820.

Figure 9:
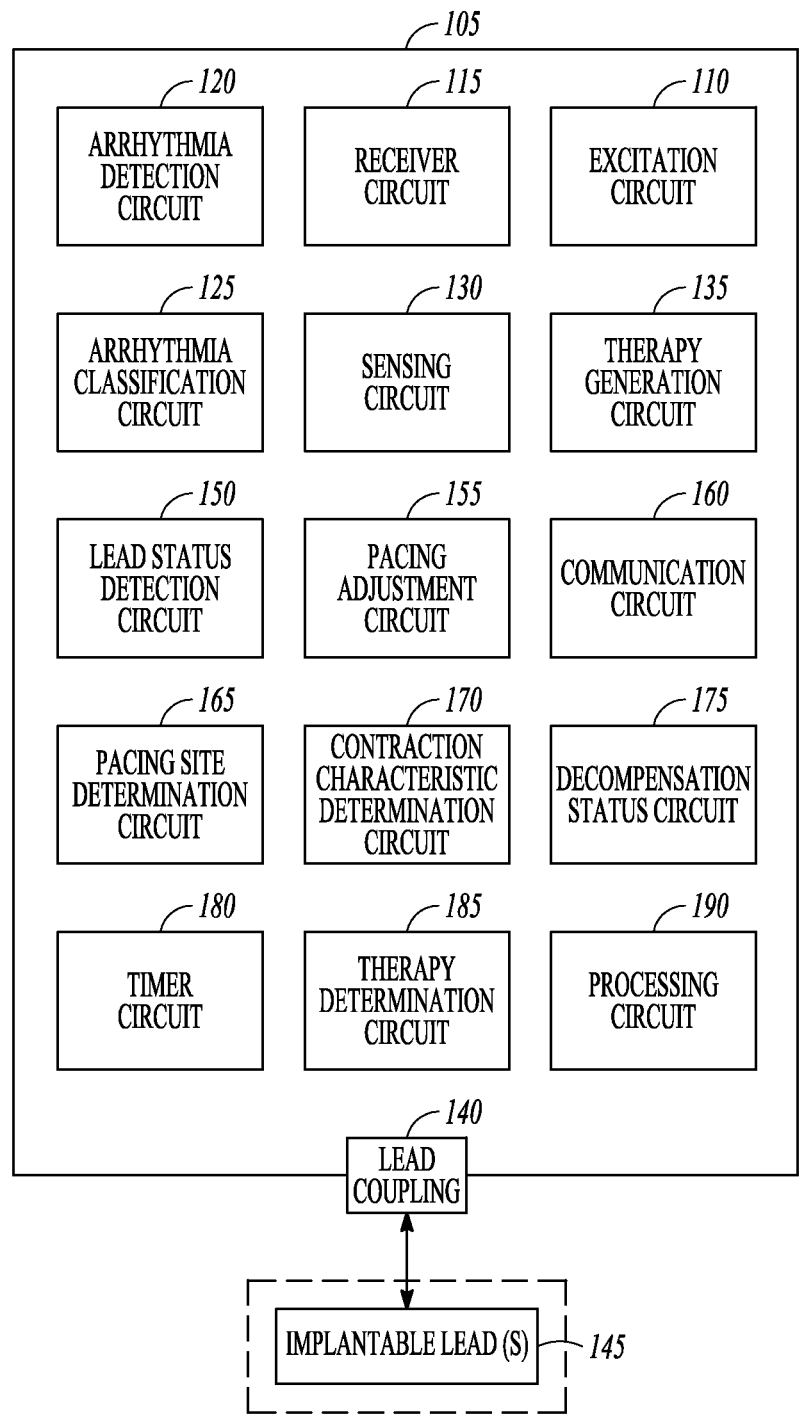
FIG. 9 illustrates generally an example of an ambulatory medical device that can be configured to analyze a signal indicative of the movement of the implantable lead.

FIG. 9 illustrates generally an example of an ambulatory medical device that can be configured to analyze a signal indicative of the movement of the implantable lead 145, such as for an indication of the movement of the heart 205 during a cardiac contraction cycle. In an example, the IMD 105 can include one or more of the excitation circuit 110, the receiver circuit 115, the arrhythmia detection circuit 120, the arrhythmia classification circuit 125, the sensing circuit 130, the therapy generation circuit 135, the lead interface connection 140, a lead status detection circuit 150, a pacing adjustment circuit 155, a communication circuit 160, a pacing site determination circuit 165, a contraction characteristic determination circuit 170, a decompensation status circuit 175, a timer circuit 180, or a therapy determination circuit 185, or a processor circuit 190.

In an example, the processor circuit 190 can include the therapy adjustment circuit configured to adjust a therapy provided by the therapy generation circuit 135. For example, the therapy adjustment circuit can be configured to adjust an anti-tachyarrhythmia pacing (ATP) therapy or a shock therapy using metrics obtained from at least one of the mechanical contraction waveform, the mechanical vibration waveform, or the signal indicative of cardiac electrical activity, as described above. The ATP therapy can be based on the current state of the subject (e.g., as indicated by one or more metrics of the mechanical contraction waveform as described above) and can permit the ATP therapy to be delivered, or can be used to trigger an extension of the ATP therapy duration as compared to a subject state where defibrillation therapy is to be delivered immediately.

In an example, an arrhythmia can be detected and classified, such as by the arrhythmia detection circuit 120 or the arrhythmia classification circuit 125, but the heart 205 is still adequately meeting the patient's metabolic demand. Such an arrhythmia can be classified as "hemodynamically stable." Often such arrhythmias can self-terminate. In such cases, a shock therapy, such as provided by the therapy generation circuit 135 to terminate the non-sustained arrhythmia, can be delayed or inhibited to avoid unnecessary shocks to the subject. In some cases, a sustained ventricular arrhythmia can be re-entrant and therefore susceptible to termination via a generated ATP therapy. The ATP therapy can be delivered to at least one pacing site (e.g., within the right ventricle) and be designed to cause a depolarization within the myocardium to terminate the arrhythmia by interfering with the timing of the re-entrant arrhythmia depolarization.

In an example, the therapy adjustment circuit can be configured to determine whether an arrhythmia is hemodynamically stable, such as by using at least one of a hemodynamic stability metric or a hemodynamic stability concordance metric. For example, the arrhythmia can be determined to be hemodynamically stable when at least one of the hemodynamic stability metric or the hemodynamic stability concordance metric meets a specified criterion (e.g., exceeds a threshold or is within a specified range).

For example, the hemodynamic stability metric or the hemodynamic stability concordance metric can be determined such as by using one or more contraction metrics (e.g., a peak determination, a peak-to-peak determination, a number of deflections within a specified duration, etc.), as described above and obtained from the mechanical contraction waveform. In an example, the hemodynamic stability metric can be determined using a central tendency of the contraction metric, such as a peak-to-peak determination, over a specified duration. In an example, the central tendency can be determined using contraction metrics that meet a specified criterion (e.g., a minute, an hour, etc.). For example, peak-to-peak determinations that exceed a specified threshold or are within a specified range can be used for computing the central tendency over the specified duration. In an example, a concordance metric can be determined using a contraction metric, as described above, obtained from one or more mechanical contraction waveforms received from at least one implantable lead 145.

The concordance metric can correspond to the concordance of the synchrony of the contraction metrics obtained from the one or more mechanical contraction waveforms. For example, determining a concordance of the metrics can be accomplished using one or more techniques, such as the techniques described in one or more of Lawrence I-Kuei Lin *A Concordance Correlation Coefficient to Evaluate Reproducibility, Biometrics* (International Biometric Society) 45 (March 1989) at 255-268, Reinhold Müller & Petra Büttner *A Critical Discussion of Intraclass Correlation Coefficients*, Statistics in Medicine 13 (23-24) (December 1994) at 2465-2476, or Klaus Krippendorff *Bivariate Agreement Coefficients for Reliability of Data*, In E. F. Borgatta and G. W. Bohnstedt (Eds.) *Sociological Methodology*, Jossey-Bass. (1970) at 139-150. The concordance metric can have a value between zero and one, where one corresponds to the highest synchrony between the contraction metrics of the mechanical contraction waveforms. In an example, the hemodynamic stability concordance metric can be determined by multiplying the concordance metric by the hemodynamic stability metric.

In an example, the therapy adjustment circuit can be configured to allow the therapy generation circuit 135 to generate an ATP therapy such as when one of the hemodynamic stability metric or the hemodynamic stability concordance metric meets a specified criterion. While the ATP therapy is being generated and the arrhythmia is still present, the therapy adjustment circuit can be configured to compute the hemodynamic stability metric or the hemodynamic stability concordance metric continuously, or at specified intervals (e.g., once per minute, etc.). In an example, the ATP therapy can be terminated by the therapy adjustment circuit determines that the arrhythmia is no longer present, or when a shock therapy is needed because the arrhythmia is no longer hemodynamically stable.

In an example, the therapy adjustment circuit can be configured such as to determine a timing of a defibrillation shock therapy. The effectiveness of a defibrillation shock delivered to myocardial tissue can depend on the local current density produced by the shock in such tissue. For example, the ability of the shock to terminate an arrhythmia can depend on the current carrying characteristics of the myocardial tissue at the location of the delivered shock (e.g., such as an RV coil located near the lateral surface of the LV apex). Generally, current densities resulting from a delivered shock can be determined using the cardiac geometry and the physical location of the myocardial tissue relative to the shock electrodes, where the current density is associated with the energy delivered over an area (e.g., an area of myocardial tissue contacting or near the shock electrode). When the myocardial tissue contracts, more of the tissue can be exposed to higher current densities than when the tissue is relaxed. For example, within the cardiac tissue, individual cardiac muscle cells are connected to form a three dimensional structure. The cardiac muscle cells (e.g., cardiac myocytes) have generally tubular shapes that shorten during a cardiac contraction to produce force. Because, more cardiac muscle cells lie within a given area (e.g., the area adjacent to the shock electrode) during the contraction, more cardiac muscle cells can be exposed to the higher current densities delivered by the shock electrode. During ventricular fibrillation, the amount of contraction of the myocardial tissue can vary over time.

In an example, a shock delivered during a cardiac contraction can require about fifteen percent lower energy to defibrillate than when the myocardial tissue is in its relaxed state. Timing the generation of a defibrillation shock to a time period during a myocardial contraction can improve the effectiveness of the shock. In an example, the therapy adjustment circuit can use an electrogram feature (e.g., a QRS complex from an electrogram received from an implantable lead 145 within the RV), or a contraction metric of a mechanical contraction waveform to time the generation of a defibrillation shock (e.g., trigger). However, if an electrogram is unavailable, the defibrillation shock can be generated asynchronously.

In an example, one or more contraction metrics (e.g., a peak-to-peak determination, a peak determination, timing information, etc.), as described above, can be determined from one or more mechanical contraction waveforms. The contraction metrics can be used by the therapy adjustment circuit to determine the timing of a generated defibrillation shock. As described above, a contraction metric can be analyzed to determine whether periodic contractions (e.g., a periodic arrhythmia) exist. A central tendency (e.g., an average, median, mean, etc.) of the contraction metric (e.g., a magnitude of a peak-to-peak deflection) can be analyzed such by comparing the central tendency to a criterion (e.g., a threshold) such as to determine whether periodic contractions exist. In an example, the central tendency can be calculated using contraction metrics meeting a criterion, such as exceeding a threshold or being within a specified range. In an example, a periodic contraction can be identified when the central tendency of the contraction metrics of the one or more mechanical contraction waveforms meet a specified criterion.

In an example, the therapy adjustment circuit can determine the timing of the defibrillation shock using one or more mechanical contraction waveforms. For example, the timing of the defibrillation shock can be determined using the contraction metrics of the mechanical contraction waveform having the largest peak-to-peak magnitudes, or using a composite mechanical contraction waveform as described above. In an example, the defibrillation shock can be timed to be generated such as when the peak-to-peak characteristic reaches a maximum value.

Additional Examples

Generally, a healthy heart can provide at least two distinct heart sounds. The first sound, "S1," is typically produced by the closing of the atrioventricular valve leaflets. The second sound, "S2," is typically produced by the closing of the semilunar valve leaflets. In a clinical setting, these events can be detected such as through cardiac auscultation by an examiner, using a stethoscope.

In some individuals, various cardiac conditions can cause additional detectable mechanical vibrations, though these may or may not be audible to the examiner. For example, a heart murmur can occur when blood is flowing harder or faster than in an otherwise healthy individual. Such a murmur can indicate a serious heart problem or merely a benign cardiac event. In another example, an "S3" sound, also known as a protodiastolic gallop, can indicate a failing left ventricle. An "S4" sound, also known as presystolic gallop, can sometimes be detected in patients exhibiting restrictive cardiomyopathy.

In addition to vibrations or sounds indicative of heart function, blood flowing through blood vessels can also produce detectable vibrations useful for diagnosis and assessment of various medical conditions. The location, velocity, and pressure of blood flow are variables that can be assessed by detection of such vibration, among other variables. Thus, mechanical vibration monitoring capabilities can be included in an implantable or an ambulatory medical device, such as to store such information for later review or analysis, or to respond to such mechanical information. For example, an individual with an implantable medical device, such as a pacemaker, can benefit from mechanical vibration monitoring, including heart sound monitoring. Such monitoring can be used for diagnosis, or an initiation or adjustment of treatment. By identifying a mechanical vibration (e.g., including one or more heart sounds), therapy can be tailored to an individual's needs, or heart sound abnormalities can be provided to a caregiver for assessment or treatment.

Implantable acoustic and mechanical transducers can be used in detecting heart and blood mechanical vibrations (e.g., including one or more heart sounds). However, the resulting acoustic information from these transducers can produce a low signal level that can be degraded by extraneous noise. Furthermore, devices having a dedicated acoustic or mechanical transducer can require additional sensors within, on, or attached to the implantable or ambulatory device, such as resulting in a greater surface area, physical volume, or number of interconnects as compared to a comparable implantable device lacking such a dedicated acoustic or mechanical transducer.

The present inventor has recognized, among other things, that mechanical information indicative of cardiac, blood, or vascular motion can be detected using a motion of one or more conductors electrically coupled to the ambulatory or implantable device. For example, the present inventors have also recognized that an implantable lead electrically and mechanically tethered to an implantable or ambulatory medical device can provide information indicative of the motion of the lead, such as using one or more electrical measurements as described in the following examples, such as to detect cardiac, blood, or vascular motion. Such information indicative of motion can also be used to time or to verify the effectiveness of a cardiac therapy (e.g., electrostimulation), in addition to diagnosing one or more cardiac conditions.

An ambulatory medical device can include an excitation circuit configured to be electrically coupled to an implantable lead, the excitation circuit configured to provide a non-tissue-stimulating first signal to the implantable lead when the implantable lead is located at or near a tissue site. In an example, the system can include a detection circuit configured to be electrically coupled to the implantable lead and configured to receive a second signal, in response to the first signal, from the implantable lead, the second signal determined at least in part by a motion of the implantable lead.

Figure 10:
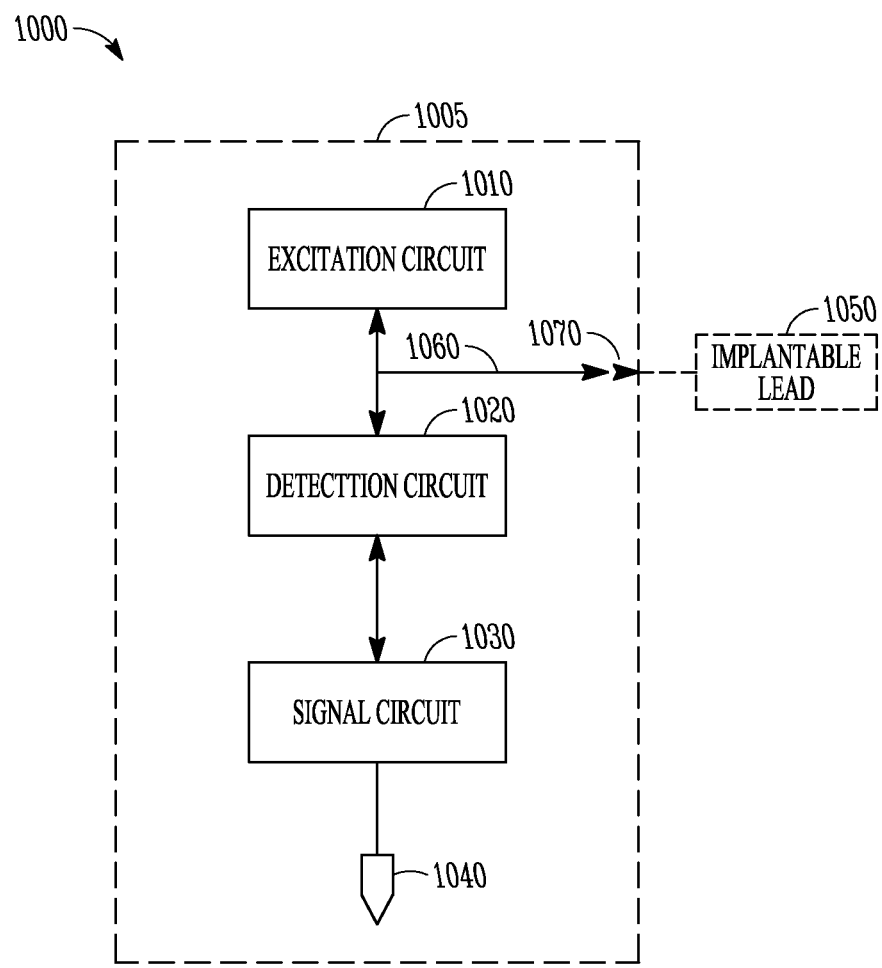
FIG. 10 illustrates generally an example of a system comprising an ambulatory medical device that can include an excitation circuit, a detection circuit, a coupling to an implantable lead, a signal processor, or an output.
Figure 19:
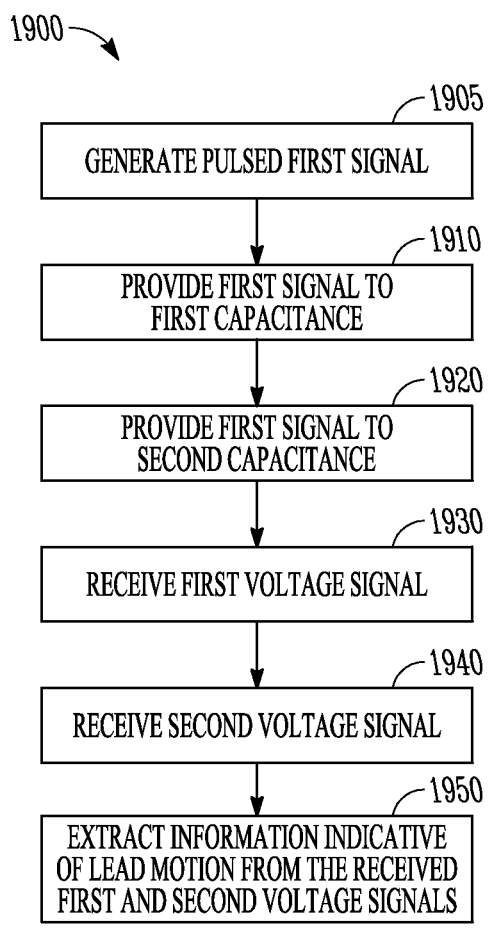
FIG. 19 illustrates generally an example that can include generating a pulsed first signal, providing the first signal to a first capacitance, providing the first signal to a second capacitance, receiving a first voltage, receiving a second voltage, or extracting information indicative of lead motion from the received first and second voltages.

FIG. 10 is a diagram illustrating generally an example of a system 1000 comprising an ambulatory medical device 1005 that can include an excitation circuit 1010, a detection circuit 1020, a signal processor 1030, an output 1040, an interconnect 1060, or a lead coupling 1070. In an example, an implantable lead 1050 can be coupled to the lead coupling 1070. One or more of the excitation circuit 1010, detection circuit 1020, signal processor 1030, output 1040, or interconnect 1060 can be realized on or within a commonly shared substrate, such as on a commonly-shared integrated circuit, module, circuit board, or the like. In another example, each block can be included in a physically separate ambulatory device, such devices coupled as shown in the example of FIG. 19, such as using one or more wired or wireless communicative couplings.

In the example of FIG. 10, the ambulatory medical device 1005 can include a cardiac stimulator, such as including pacing or cardiac resynchronization therapy (CRT) circuitry configured to deliver pacing or resynchronization energies to cardiac tissue. In an example, the ambulatory medical device 1005 can include a neural stimulator device, such as to provide electrical, mechanical, optical, acoustic or chemical stimulation to one or more neural targets.

In the example of FIG. 10, the excitation circuit 1010 can be coupled to a detection circuit 1020. The excitation circuit 1010 generally provides an excitation energy, such as including a first signal. In an example, the first signal can include an oscillating electrical signal, such as a time-varying voltage or current. In an example, the first signal can include a pulsed electrical signal, such as including one or more current or voltage pulses including a specified amplitude, duration, pulse repetition rate, duty cycle, or morphology, among other parameters. In an example, the excitation circuit 1010 can be coupled to the lead coupling 1070 via interconnect 1060, such as using a header or other connector included as a portion, part, or component of the ambulatory medical device 1005.

In the example of FIG. 10, an implantable lead 1050 can be coupled to the lead coupling 1070. For example, the implantable lead 1050 can include one or more conductors. In an example, the implantable lead 1050, such as coupled to the implantable lead coupling 1070, can be located at a site within or on the body (e.g., including one or more surface, subcutaneous, or intravascularly-located electrodes or conductors). In an example, the implantable lead 1050 can be implanted or otherwise place within a body, such as within or near a heart, either temporarily or more permanently, such as for ambulatory monitoring or therapy delivery.

In the example of FIG. 10, the detection circuit 1020 can be coupled both to a signal processor 1030 and the lead coupling 1070 via a commonly-shared interconnect 1060. In an example, the implantable lead 1050, or an external lead, can be coupled to the lead coupling 1070. In an example, the detection circuit 1020 can be configured to receive a second signal provided by the implantable lead 1050. For example, the detection circuit 1020 can be configured to interpret or processes the first signal, such as by providing the first signal to the implantable lead 1050 before or during receiving the second signal.

In the example of FIG. 10, the detection circuit 1020 can be configured to receive a second signal, such as from the implantable lead 1050 via the lead coupling 1070 and the interconnect 1060 (e.g., in response to the first signal). In an example, the detection circuit 1020 can be configured to interpret and process a received second signal before transmitting the received second signal to the signal processor 1030. For example, the detection circuit 1020 can be configured to determine a first characteristic of the second signal (e.g., information about an amplitude, frequency, noise floor, signal-to-noise ratio, or one or more other characteristics). In an example, the amplitude characteristic of the second signal can be compared to a threshold value, and the result of the comparison can be used to determine if the received second signal can be further processed by the signal processor 1030. For example, if the amplitude of the second signal meets or exceeds a threshold value, the detection circuit 1020 can be configured to transmit the second signal to the signal processor 1030 for further analysis. Conversely, if the amplitude of the second signal is below the threshold value, the detection circuit can withhold transmission of the second signal or otherwise indicate to the signal processor 1030 that further analysis should be withheld (e.g., if the second signal is so low in amplitude that extraction of motion information would be difficult).

In the example of FIG. 10, the signal processor 1030 can be coupled to the detection circuit 1020 and the output 1040. In an example, the signal processor 1030 can be configured to receive information derived from the second signal. The signal processor 1030 can be configured to extract from the second signal information indicative of motion of the implantable lead 1050. Such motion of the implantable lead 1050 can include a physical displacement of any constituent element of implantable lead 1050 with respect to an equilibrium position. In an illustrative example, the implantable lead 1050 can experience a physical displacement because the implantable lead is mechanically coupled to a vibrating tissue, such as implanted within or near contractile tissue in the heart. In an example, the information indicative of motion of the implantable lead 1050 can include audible or acoustic information such as provided by a heart sound, or other higher or lower-frequency mechanical information not necessarily within the audible frequency spectrum.

In an example, information indicative of motion of the implantable lead 1050 can include impedance information, such as including a change in lead impedance determined at least in part by mechanically coupling cardiac or vascular mechanical vibrations to the implantable lead 1050. For example, impedance information can be interpreted by the signal processor 1030 to detect, classify, or monitor one or more physiological events. Such physiological events can include the closing of the atrioventricular or semilunar valve leaflets in the heart.

In the example of FIG. 10, the output 1040 can be coupled to the signal processor 1030. In an example, the output 1040 can receive information from the signal processor 1030. The received information can be passed through an output 1040 to one or more other portions, parts or components of the ambulatory medical device 1005. In an example, the output 1040 can be coupled to another device via a wired or wireless communicative connection (e.g., to transfer information to one or more other implantable or ambulatory devices, or to an external assembly). In an example, the signal processor 1030 can perform one or more signal adjustments such as impedance or level adjustments, among others, before providing the lead motion information to the one or more other portions via the output 1040.

Figure 11:
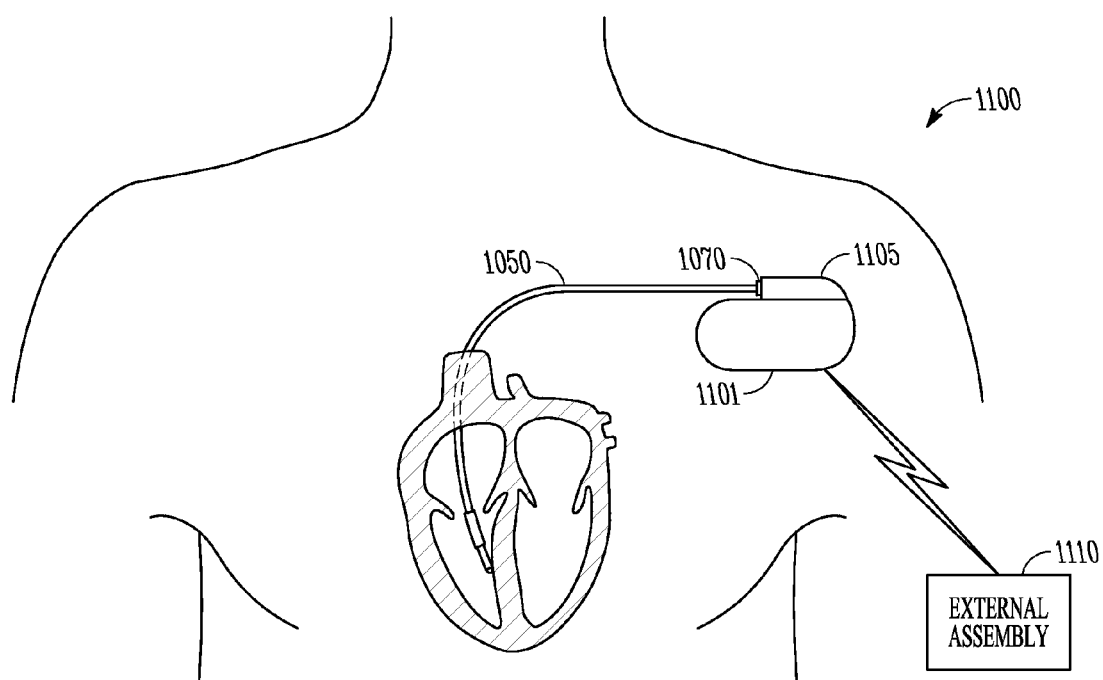
FIG. 11 illustrates generally an example of a portion of a system that can include an implantable medical device, an implantable lead, or a communicative coupling between the implantable medical device and an external assembly.

FIG. 11 illustrates generally an example of a system 1100 that can include an implantable medical device 1105. In this example, the implantable medical device 1105 can include one or more implantable lead couplings, such as a lead coupling 1070. In certain examples, the implantable medical device 1105 includes a hermetically-sealed or similar housing 1101 coupled to the implantable lead coupling 1070. For example, the housing 1101 can include titanium or other biocompatible material, such as one or more other conductive materials.

In the example of FIG. 11, the system 1100 can include an implantable lead 1050 implanted in a heart, such as implanted endocardially via an intravascular route from one or more of a subclavian vein or a femoral artery. In an example, the implantable lead 1050 can include one or more conductors, such as one or more concentric or laterally-separated conductors. In an example, one or more conductors can include a braided or coiled shield conductor. The one or more conductors can be insulated from one another and from the environment surrounding the implantable lead 1050, such as using a silicone or a poly-ether-ether-ketone (PEEK) insulation, among others. In an example, the conductors to be used for mechanical vibration sensing can be selected based on measurement of RF coupling or an AC impedance between the conductors. Such RF coupling or impedance measurements can be used to determine a conductor pair or combination likely to exhibit higher mechanical vibration sensitivity than other pairs or combinations. Such measurements can also be used to find a conductor pair or combination including an input impedance most closely matched to a conjugate of the output impedance of one or more of a detection circuit, excitation circuit, or interconnect as shown in FIG. 10, and FIGS. 12-14.

In an example, the implantable medical device 1105 can be configured to communicate with the external assembly 1110. The communication between the implantable medical device 1105 and an external assembly 1110 can be wireless or through a wired connection, or using one or more other communication schemes (e.g., using an optical communication link or an acoustic communication link, among others). For example, the external assembly 1110 can be a portion or part of a patient management system, such as including or in communication with one or more remote or web-based clients communicatively coupled to one or more servers comprising medical and patient databases.

In an example, the implantable medical device can include one or more of a pacemaker, a defibrillator, an implantable monitor, a drug delivery device, a cardiac resynchronization therapy device, a neural stimulation device, or one or more other implantable assemblies configured to monitor a person or configured to provide one or more treatments to the person. Such monitoring or treatment can include, among others, electrostimulation of tissue such as cardiac tissue, or electrical monitoring of muscular or cardiac activity, among others.

Figure 12:
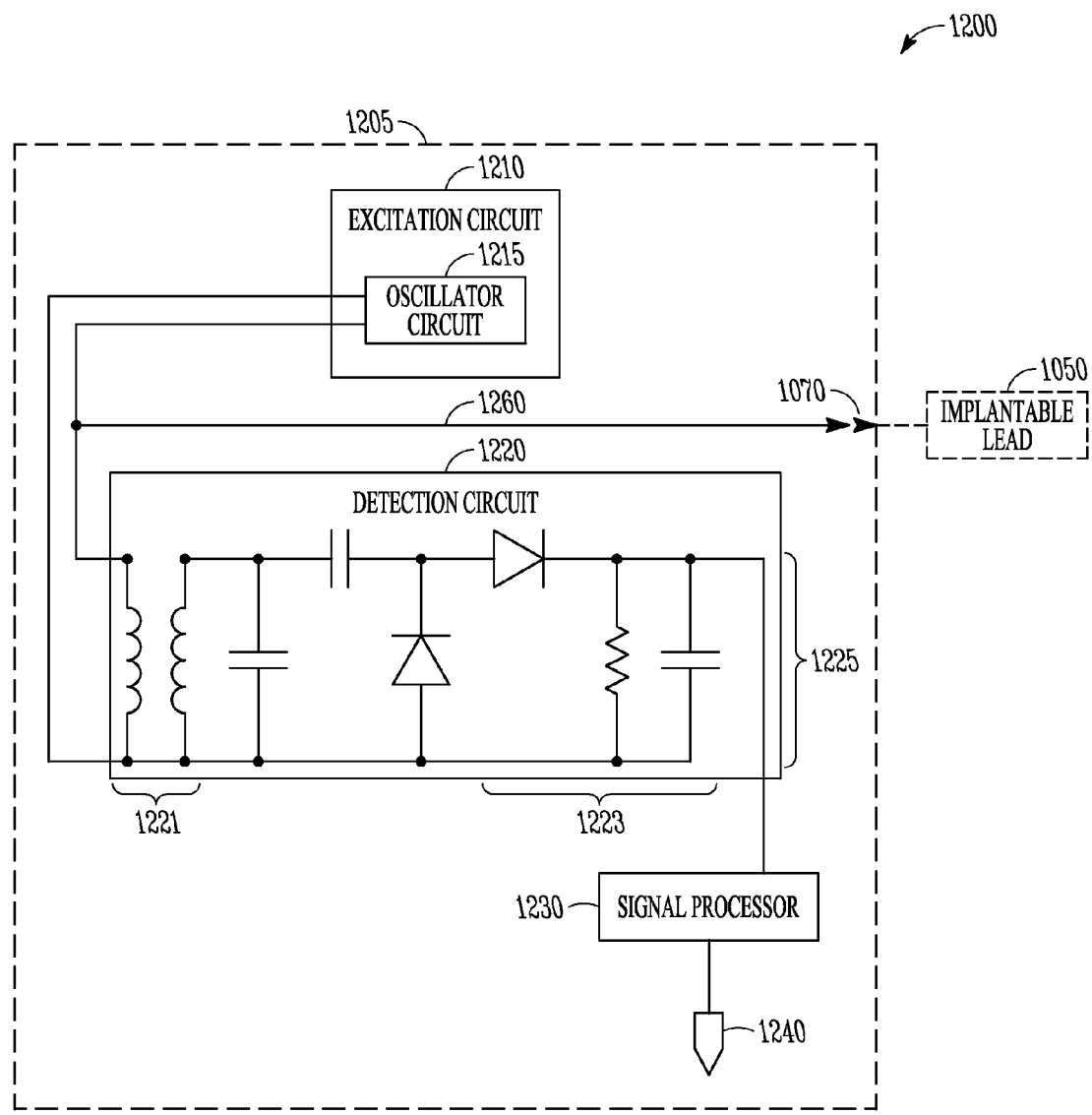
FIG. 12 illustrates generally an example of a portion of a system comprising an excitation circuit that can include an oscillator circuit, a detection circuit, a coupling to an implantable lead, a signal processor circuit, or an output.

FIG. 12 illustrates generally an example of a system 1200 that can include an ambulatory medical device 1205, such as including an implantable device as shown in the example of FIG. 11, an externally-worn assembly, or a combination of implantable and external portions. In this example, an excitation circuit 1210 can include an oscillator circuit 1215 such as configured to provide a first signal. In an example, the oscillator circuit can provide an RF signal (e.g. from about 10 to about 30 MHz), such as including a specified current level.

In an example, an interconnect 1260 can be coupled to one or more of the excitation circuit 1210 or a detection circuit 1220. In this example, the first signal (e.g., an excitation current signal) can be provided by the excitation circuit 1210 to develop a voltage across two conductors included in the lead coupling 1070 via the interconnect 1260. For example, the first signal can include one or more current signals provided to one of the conductors, and received from the other conductor. The detection circuit 1220 can be configured to receive a second signal (e.g. a developed voltage) across the lead coupling 1070.

In an example, the detection circuit 1220 can include a demodulation circuit 1225. The demodulation circuit 1225 can include an envelope detector 1223 or a tuned resonant transformer 1221 that can be impedance-matched to one or more other attached components. In an example, the envelope detector 1223 can demodulate or extract a relatively low frequency component of time-varying voltage from the second signal, such as containing information indicative of motion of an implantable lead 1050 attached to the lead coupling 1070. The demodulation circuit 1225 can be coupled to a signal processor 1230. In an example, the signal processor 1230 can be configured to extract information indicative of motion of the implantable lead 1050, such as including protodiastolic or presystolic gallop sounds, or other mechanical vibrations such as indicative of blood flow, or pressure, among others.

In an example, additional elements can be included in the system 1200 to enhance sensitivity or provide additional mechanical event information. For example, multiple implantable leads can be implanted in multiple locations within or on a body and lead motion information can be collected from one or more of the multiple locations. For example, a second lead comprising at least one electrical conductor can be coupled to a second lead coupling, or the implantable lead 1050 can include multiple electrical conductors that can be coupled to one or more lead couplings. In an example, one or more mechanical events can provide a change in the impedance of the system comprising the multiple conductors, such as detectable using the second signal provided in response to the first signal. In an example, the signal processor 1230 can be coupled to an output 1240, and extracted information indicative of motion of the implantable lead 1050 can be communicated to another assembly via the output 1240. Such other assemblies can include, among others, an additional ambulatory medical device located internally or externally to a body, or an external assembly 1110, a combination of one or more implantable and external assemblies.

Figure 13:
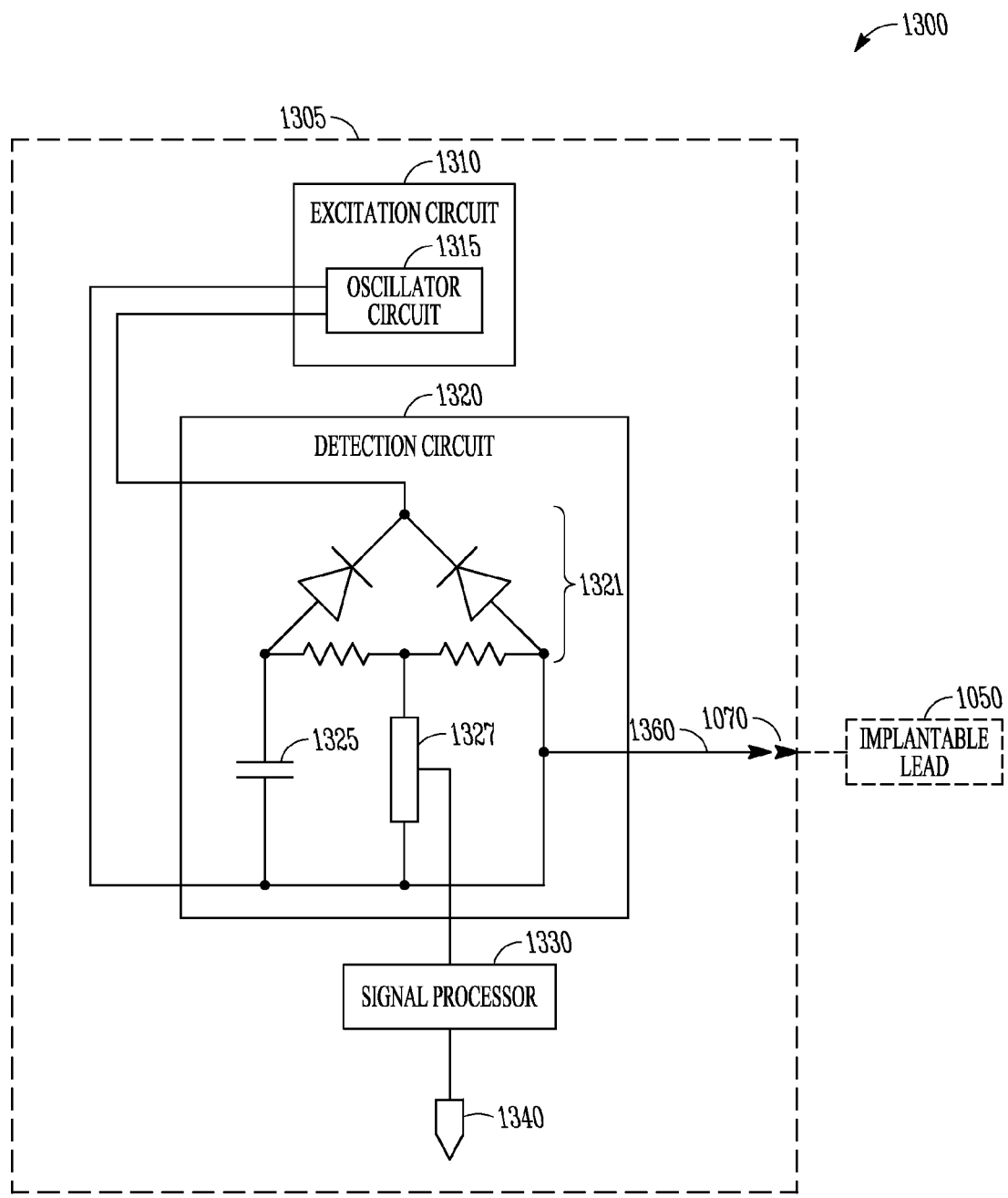
FIG. 13 illustrates generally an example of a portion of a system comprising an excitation circuit that can include an oscillator circuit, a detection circuit comprising a coupling to an implantable lead and a bridge circuit, a signal processor circuit, or an output.

FIG. 13 illustrates generally an example of a system 1300 including ambulatory medical device 1305, such as including an implantable device as shown in the example of FIG. 11, an externally-worn assembly, or a combination of implantable and external assemblies. In this example, an excitation circuit 1310 can include an oscillator circuit 1315 configured to provide a first signal, such as provided to a portion of a detection circuit 1320. In an example, an interconnect 1360 can be coupled to the detection circuit 1320. The detection circuit 1320 can include a bridge circuit 1321, a capacitive element 1325, or an envelope detector 1327, among other components or portions. In the example of FIG. 13, the sensitivity of detection circuit 1320 can vary with respect to a specified excitation frequency. In an illustrative example, the oscillator circuit 1315 can provide a first signal including a sine wave signal with a frequency of around 100 KHz to 1 MHz (or including one or more other frequencies). The bridge circuit 1321 can include one or more diodes or other rectifiers exhibiting low forward resistance, such as one or more germanium diode (e.g. type 1N60). In this example, the bridge circuit 1321 can include resistors of about the same values. The implantable lead 1050 can provide a capacitance, and the capacitive element 1325 can include a specified capacitance value approximately equal to the capacitance provided by the implantable lead 1050 when implantable lead 1050 is in equilibrium (e.g., relatively motionless, or subject to a specified baseline of vibration or motion). The capacitance provided by the implantable lead 1050 can be one or more capacitances provided between two or more conductors, such as included in a single implantable lead 1050, or between conductors respectively included in two or more implantable leads. Generally, the one or more capacitances can be provided by a combination of multiple conductors, and such capacitances can be combined in a series or parallel configuration, such as each including a capacitance contribution from one or more pairs of conductors. In an example, the capacitance can be provided between conductors of physically separate implantable leads. Such lead capacitance can vary in proportion or with respect to motion or vibration coupled to the lead such as from surrounding tissue or blood motion. In an example, the envelope detector 1327 can include a relatively high input impedance to achieve a specified sensitivity of the system 1300. The envelope detector 1327 can include one or more of a diode or rectifier detector, or a synchronous detector, such as to improve noise rejection, selectivity, or one or more other characteristics.

In an example, a signal processor 1330 can be configured to receive a signal from the detection circuit 1320, such as provided at least in part by the envelope detector 1327. For example, the signal processor 1330 can be configured to extract information from the received voltage signal indicating a motion of an implantable lead 1050. In an example, the signal processor 1330 can include a low pass filter circuit to process the signal received from the detection circuit 1320. In an example, the signal processor 1330 includes an amplification circuit, or one or more other circuits or components, such as to amplify the received signal. In an example, the signal processor 1330 can include an analog-to-digital converter to convert the information indicative of motion into a digital data signal, such as for storage, further processing, or for presentation to a caregiver or clinician.

In an example, an output 1340 can be configured to receive a signal from the signal processor 1330, and the output 1340 can be configured to transfer the information indicative of motion of the implantable lead 1050 to another implantable or ambulatory medical device, or to an external assembly such as the external assembly 1110 using a wireless or wired communicative coupling. In an example, the output 1340 can be configured to communicate with one or more external assemblies including one or more tabletop or handheld electronic devices (e.g. a cell phone, smart phone, tablet, laptop, or personal digital assistant (PDA), among others), in addition to or instead of one or more external assemblies dedicated for medical diagnosis or assessment.

In an illustrative example, one or more of the detection circuit 1320 or the signal processor 1330 can receive a second signal in response to the first signal, and the second signal can include a portion in-phase with the first signal, and a second portion in quadrature (e.g., ninety degrees out of phase) with the first signal. In this illustrative example, the detection circuit 1320 or the signal processor 1330 can use the quadrature component of the second signal to determine the change in capacitance of the lead system, thus canceling out the effect of the resistive component of an impedance presented by the lead 1050 to the measurement circuit.

Figure 14:
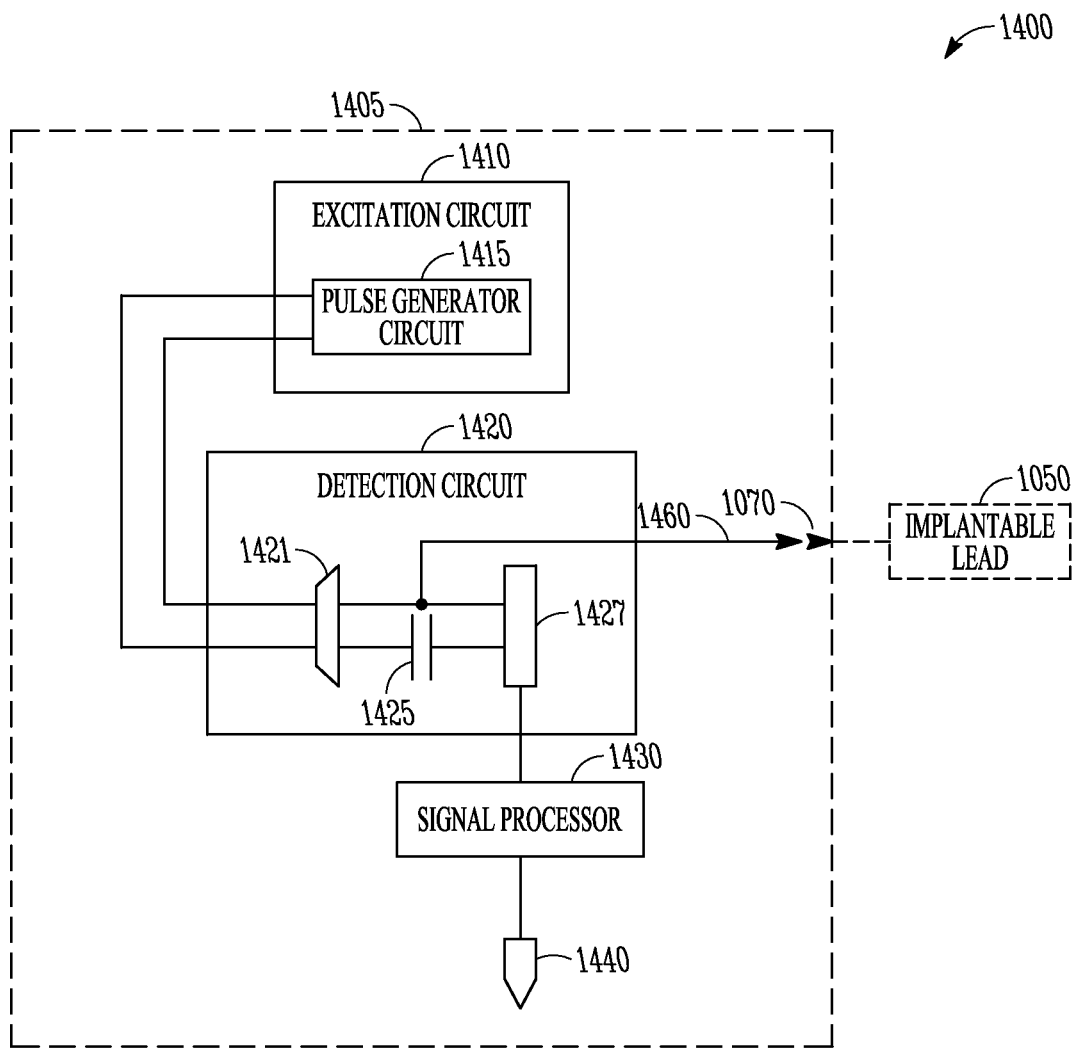
FIG. 14 illustrates generally an example of a portion of a system that can include an excitation circuit such as including a pulse generator circuit, a detection circuit including a coupling to an implantable lead and a voltage detector, a signal processor circuit, or an output.

FIG. 14 illustrates generally an example of a system 1400 including ambulatory medical device 1405, such as including an implantable device as shown in the example of FIG. 11, or an externally-worn assembly. In this example, an excitation circuit 1410 can include a pulse generator circuit 1415 configured to provide a first signal, and a detection circuit 1420. In an example, the detection circuit 1420 can include a multiplexer 1421, a capacitive element 1425, or a voltage detector 1427. In an example, the multiplexer 1421 can be configured to select among one or more inputs, wherein the inputs can be coupled to the excitation circuit 1410, or another signal-generating source. In an example, the multiplexer 1421 can be under the control of the detection circuit 1420 or another component of the ambulatory medical device 1405. An interconnect 1460, the voltage detector 1427, or a lead coupling 1070, among other components, can be coupled to the multiplexer 1421.

One or more portions of the system 1400, such as the interconnect 1460, multiplexer 1421, or voltage detector 1427, can be implemented on a rigid or flexible circuit board, such as including one or more application specific integrated circuits, among other components. In an example, the lead coupling 1070 can be implemented via an electrical and mechanical interconnect in a header block that can be attached to the housing 1101 of an implantable medical device housing, such as shown in FIG. 11. The housing 1101 of the implantable medical device itself can be used as one of the conductors for capacitance or impedance measurement.

In an example, the excitation circuit 1410 can be coupled to the multiplexer 1421. In an example, the multiplexer 1421 can be configured to couple the excitation circuit 1410 to each of the interconnect 1460 and the capacitive element 1425, concurrently or successively. In an example, the concurrent or successive coupling can be performed by the multiplexer 1421 under the direction of a logic circuit included as a portion of the detection circuit 1420. For example, the logic circuit can include a counter or timer such as to provide one or more counts or durations to be used by the logic circuit to switch the state of the multiplexer 1421, such as after a specified duration of time elapses as indicated by the counter or timer. In an example, the logic circuit can be configured to count a number of pulses provided by the excitation circuit 1410. In this example, the logic circuit can be configured to switch the state of the multiplexer 1421, such as after a specified count of a number of pulses is met or exceeded as indicated by the counter.

In the example of FIG. 14, the multiplexer 1421 can be configured to couple the first signal to a first capacitance provided by implantable lead 1050. In an example, a first voltage can be developed across the first capacitance in response to the first signal. A second signal that includes the first voltage can be received by the voltage detector 1427. In this example, a signal processor 1430 can receive the output of the voltage detector 1427. In an example, the signal processor 1430 can be configured to compare the received signal from the first capacitance to a threshold voltage (e.g., monitoring a charging of the first capacitance to reach the specified threshold voltage).

In the example of FIG. 14, the multiplexer 1421 can be configured to couple the first signal to a second capacitance provided by the capacitive element 1425 (e.g., a "reference capacitance," charged using the same or a similar first signal). In an example, the multiplexer 1421 can be configured to provide the first signal to each of the first capacitance and second capacitance, either separately, sequentially, or in combination. In an example, a second voltage can be developed across the second capacitance in response to the first signal. In an example, the second signal that includes the second voltage can be received by the voltage detector 1427. In this example, a signal processor 1430 can receive the output of the voltage detector 1427. In an example, the signal processor 1430 can be configured to compare the received signal from the second capacitance to the specified threshold voltage (e.g., monitoring a charging of the second "reference" capacitance to reach the specified threshold voltage).

In the example of FIG. 14, the signal processor 1430 can be configured to determine a relative indication of information (e.g., a ratio, a difference, etc.) derived from one or more of the first or second voltages measured with respect to the first or second capacitances. Coupling of mechanical vibration to the implantable lead 1050, or other motion of the lead, can cause a detectable change in the capacitance of the lead. For example, the second signal received from the first capacitance can differ from the second signal received from the second capacitance in response to a similar excitation by the first signal. In this manner, a variation between a reference capacitance (e.g., provided by capacitive element 1425) and the capacitance of the lead can be used to provide information corresponding to motion of the implantable lead. In an example, capacitive element 1425 can include, among other things, an additional specified capacitance such as provided by a discrete capacitor, a second implantable lead, or combination of conductors, a number of interconnected implantable leads, or a capacitive transducer.

In the example of FIG. 14, the first signal can charge the first capacitance to a first specified threshold voltage, and a corresponding duration of the charge time can be determined (e.g., such as when the first capacitance is charged using a sequence of current pulses or a constant current). In an example, the voltage detector 1427 can be configured to receive the first voltage in response to the charging of the first capacitance. In this example, the signal processor 1430 can be configured to determine a duration of a first charge time, corresponding to a duration where the first voltage is between a lower threshold (e.g., around 0 Volts), and an upper threshold (e.g., the first specified voltage threshold). In an example, the signal processor 1430 can be configured to determine a duration of a second charge time, corresponding to a duration where the second voltage is between the lower and upper thresholds. If the capacitance of the capacitive element 1425 and the lead capacitance are roughly equal, the determined first and second charge times can be roughly equal, such as when the lead 1050 is at rest or equilibrium.

In the example of FIG. 14, the excitation signal (e.g., the first signal), can include a series of current pulses having a specified peak current level, duration, pulse repetition rate, duty cycle, etc. The signal processor 1430 can be configured to count a number of pulses delivered to the lead 1050, or to a capacitive element 1425. For example, the voltage detector 1427 can be configured to receive pulsed signals and the signal processor 1430 can be configured to count the received pulsed signals. In an example, the signal processor 1430 can be configured to count a first count of a number of pulses provided to the first capacitance, such as to reach the specified threshold voltage (e.g., the pulse count can be a proxy for a measurement of a charge time duration, such as when pulses of determinable width and level are used). In an example, the signal processor 1430 can be configured to extract from the first count an indication of lead motion, since the variation in the lead capacitance can provide a difference in a number of pulses needed to reach the specified threshold, such as compared with a baseline number of pulses corresponding to a lead at rest or in equilibrium.

In an example, the sensitivity of the system 1400 can be enhanced by using a comparison between a second capacitance (e.g., a reference capacitance or another pair or combination of lead conductors) and the capacitance of the lead 1050. The signal processor 1430 can be configured to count a second count of a number of pulses provided to the second capacitance (e.g., using a series of pulses of determinable width or level, as above). For example, the signal processor 1430 can be configured to extract from the first and second counts a relative indication of information that can indicate lead motion (e.g., a difference, or ratio, etc., between the first and second counts of pulses). In an illustrative example, the signal processor 1430 can measure multiple pulse durations and perform comparison operations, such as including using one or more techniques disclosed in Pelletier et al. U.S. Pat. No. 4,011,500 entitled "PHYSICAL DISPLACEMENT SENSING WITH DIFFERENTIAL CAPACITOR," which is hereby incorporated by reference in its entirety, including its disclosure of using a differential capacitor to detect a physical displacement.

In an example, an output 1440 can be configured to receive information from the signal processor 1430, and to transfer such information to one or more other portions of the ambulatory medical device 1405, or to communicate with an external assembly.

Figure 15:
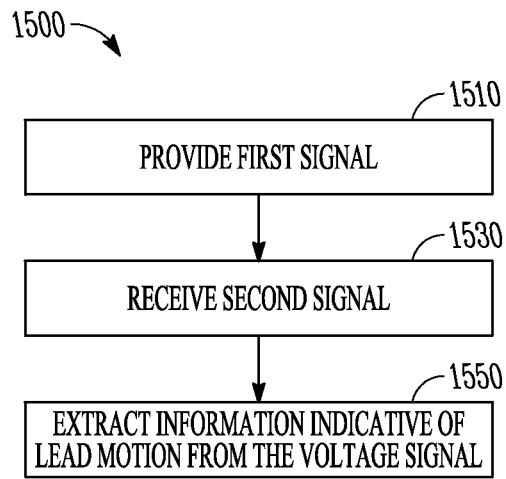
FIG. 15 illustrates generally an example that can include providing a first signal, receiving a second signal, or extracting information indicative of lead motion from the second signal.

FIG. 15 illustrates generally an example 1500 that can include providing a first signal, receiving a second signal, or extracting information indicative of lead motion from the second signal, such as using circuitry or techniques as discussed above in the examples of FIGS. 10-14.

At 1510, a first signal can be provided to excite the ambulatory medical device 1005. In an example, the first signal can be a non-tissue-stimulating electrical signal. For example, the first signal can be an AC signal generated or provided by an excitation circuit 1010. In an example, the first signal can be provided to an implantable lead 1050.

At 1530, a second signal can be received in response to the first signal. In an example, the detection circuit 1020 can be configured to receive the second signal from the implantable lead 1050. In an example, the second signal can include, among other signals, a phase-shifted or modulated version of the first signal, a voltage signal, a logic signal, or a data signal including information indicative of motion of the implantable lead.

At 1550, information can be extracted from the second signal. The extracted information can indicate motion of the implantable lead 1050. In an example, the information can indicate a relative or absolute indication of a displacement of the implantable lead 1050. In an example, the information can include an electrical representation of mechanical vibration or motion coupled to the lead, such as including a heart sound, a blood pressure sound, or respiratory sound, among others.

Figure 16:
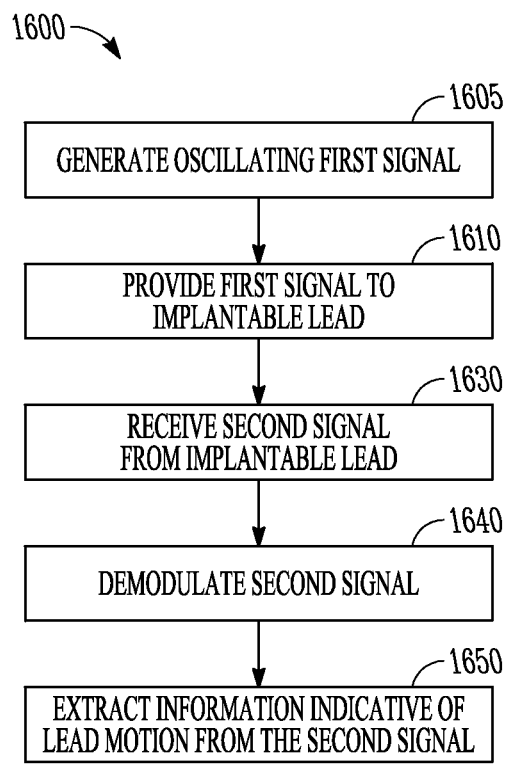
FIG. 16 illustrates generally an example that can include generating an oscillating first signal, providing the first signal to an implantable lead, receiving a second signal from the implantable lead, demodulating the second signal, or extracting information indicative of lead motion from the second signal.

FIG. 16 illustrates generally an example 1600 that can include generating an oscillating first signal, providing the first signal to an implantable lead, receiving a second signal from the implantable lead, demodulating the second signal, or extracting information indicative of lead motion, such as using circuitry or techniques discussed above with respect to FIGS. 10-14.

At 1605, a first signal can be generated by an oscillator circuit included in an excitation circuit 1010. In an example, the oscillator circuit can include a Colpitts oscillator. In an example, the first signal can include an AC signal and the frequency of oscillation can be tunable such as to achieve a specified sensitivity.

At 1610, the first signal can be provided to the implantable lead 1050, such as via an interconnect 1260 and a lead coupling 1070. In an example, the first signal can be coupled through a series capacitor with high DC or near-DC impedance to create a relatively constant current signal into the implantable lead 1050. In an example, a change in capacitance of the implantable lead 1050 can modulate the impedance of the circuit comprising the implantable lead 1050, the lead coupling 1070, and the interconnect 1260.

At 1630, a second signal can be received from the implantable lead 1050, such as in response to the first signal. In an example, the modulated impedance of the circuit comprising the implantable lead 1050, the lead coupling 1070, and the interconnect 1260 can produce the second signal in response to the first signal such that the second signal can be different than the first signal.

At 1640, the second signal can be demodulated to recover the information indicative of lead motion. In an example, the second signal can be received by a detection circuit 1220 wherein a demodulation circuit 1225 can be used to demodulate the received second signal. The demodulation circuit 1225 can include a tuned resonant transformer 1221 or an envelope detector 1223, wherein the transformer 1221 can be configured to provide an impedance-matched coupling between the second signal and the envelope detector. In an example, the second signal can include a voltage that can be detected between conductors in the implantable lead 1050, including a voltage that can include a phase-shifted version of the first signal. In this example, information indicative of lead motion can be realized by extracting a relatively low frequency component of a time-varying voltage from the second signal using the envelope detector 1223. In an example, the second signal comprises a large DC voltage with a small AC voltage superimposed, wherein the AC voltage can result from the response of the first signal to the modulated impedance. In an example, the implantable lead 1050 can be implanted in a heart and provided with the first signal. In this example, the resulting AC component of the second signal can include information about heart wall motion (or information indicative of one or more other mechanical vibrations coupled to the lead 1050).

At 1650, information can be extracted from the demodulated second signal that can indicate motion of the implantable lead 1050. In an example, the second signal can be received from the implantable lead 1050. In an example, the second signal can be relatively constant over time (e.g., relatively constant in frequency or in amplitude, among other parameters) for a stationary or immobilized implantable lead 1050 because the impedance of the implantable lead 1050 can remain relatively unchanged at equilibrium. However, as the implantable lead 1050 undergoes movement (or as mechanical vibration is coupled to the lead), the movement of the implantable lead 1050 can modulate or change the impedance of the system containing the one or more conductors in the implantable lead 1050, and the second signal can deviate from its relatively constant amplitude or frequency. For example, a mechanical vibration coupled to the implantable lead 1050 can produce a microphonic effect such as receiving the vibration information by the implantable lead 1050 and providing a second signal in response to the first signal that is analogous to the received vibration. In this example, the mechanical vibration is effectively translated to an analogous electrical signal.

In an example, more than one implantable lead can be included in the ambulatory medical device 1200, as previously described. In this example, the first signal can be provided to the system comprising the multiple implantable leads and the second signal can be received from the same system. In an example, the relative or independent motion of the two or more leads can modulate the impedance of the system comprising the leads. In an example, the additional leads can provide a greater magnitude of impedance modulation of the system comprising the sensing elements, therefore exaggerating the response signal under some circumstances (e.g., using a "differential" measurement of multiple lead impedances or capacitances). Under some other set of circumstances, the impedance modulation of the system comprising the multiple sensing elements may have a nullifying effect on the response signal. In such an example, the implantable leads can be implanted or configured, or the conductors used for sensing can be selected, in such a manner as to create a specified response or sensitivity.

In an example, the demodulated signal can be provided to a signal processor 1230 for further extracting the information indicative of motion of the implantable lead 1050. In an example, the second signal can be high pass filtered to remove the low frequency wall motion and isolate higher frequency blood flow motion information. In this example, the pitch of the resulting signal can be related to the velocity of the blood flow. In an example, a demodulated and filtered signal can be transmitted, such as via an output 1240, to an external assembly, such as for visual or audible presentation to a clinician or care giver, such as using an audio amplifier. In an example, an examiner can listen to the blood flow information or the heart wall motion information provided by the medical device. For example, when the information indicative of motion includes a subsonic or ultrasonic component, such components can be respectively upconverted or downconverted (e.g., adjusted in speed or frequency) for playback using an audible range of frequencies.

Figure 17:
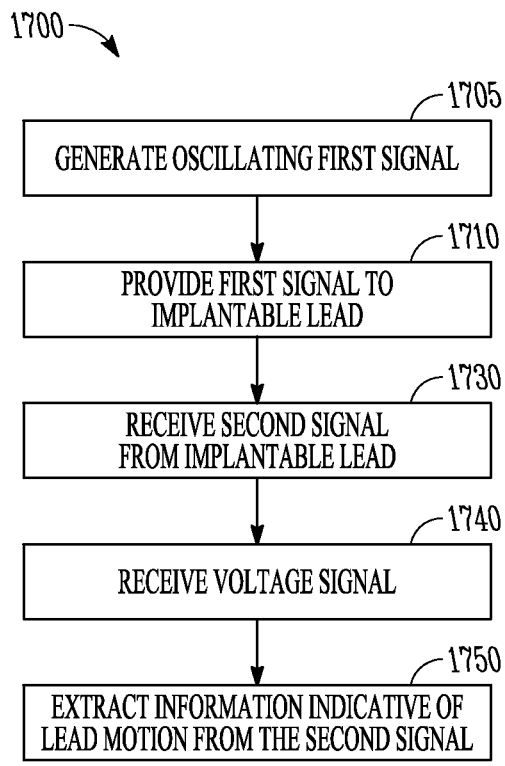
FIG. 17 illustrates generally an example of a portion of a method such as including generating an oscillating first signal, providing the first signal to an implantable lead, receiving a second signal from the implantable lead, receiving a voltage, or extracting information indicative of lead motion from the received voltage.

FIG. 17 illustrates generally an example 1700 that can include generating an oscillating first signal, providing the first signal to an implantable lead, receiving a second signal from the implantable lead, receiving a voltage signal, or extracting information indicative of lead motion from the voltage signal, such as using circuitry or techniques discussed above with respect to FIGS. 10-14.

At 1705, a first signal can be generated by an oscillator circuit included in excitation circuit 1010. In an example, the oscillator circuit can include a Pierce oscillator. In an example, the frequency of oscillation can in part determine the sensitivity of a system 1300. The frequency of the first signal can be specified to correspond to one or more frequencies that exhibit a change in impedance of an implantable lead 1050 at least in part due to motion of the implantable lead 1050.

At 1710, a first signal can be provided to the implantable lead 1050. In an example, the first signal can be an AC signal routed through a bridge circuit 1321. In this example, the implantable lead 1050 can form a portion (e.g., one of the legs) of the bridge circuit 1321. In an example, a capacitive element 1325 forms the leg of the bridge circuit 1321 that is opposite the implantable lead 1050. In an example, positive half cycles of the first signal can charge a first capacitance provided by the implantable lead 1050. In an example, the capacitive element 1325 can act as a second capacitance, which can be charged during negative half cycles of the first signal.

At 1730, a second signal can be received from the implantable lead 1050 wherein the second signal can be a response to the first signal. In an example, the second signal can be a voltage signal indicating a voltage across the first capacitance, and thus a change in capacitance of the implantable lead 1050 can be transformed into a voltage signal. The second signal can be a voltage signal indicating a voltage across the second capacitance.

At 1740, the voltage signal can be received. In an example, a voltage signal indicating a change in capacitance can be received by the envelope detector 1327. In an example, the envelope detector 1327 can be a diode or rectifier detector or a synchronous detector operating at the same frequency as the first signal. In an example, the voltage across the envelope detector 1327 can include a relatively constant value (e.g., amplitude or frequency) when the implantable lead 1050 is at equilibrium. However, when the capacitance of implantable lead 1050 changes, such as during a movement of the implantable lead 1050, the voltage across the envelope detector 1327 can change by an amount proportional to the displacement of the implantable lead 1050, the magnitude of the change in capacitance indicative of displacement.

At 1750, information can be extracted from the envelope detector 1327 that can be indicative of motion of the implantable lead 1050. In an example, a signal can be transmitted to an external source and amplified by an audio amplifier. In an example, an examiner can listen to heart sound information, as discussed above in the example of FIG. 16. In an example, heart wall motion information can be isolated and visually or audibly presented to the examiner (e.g., a clinician or caregiver).

Figure 18:
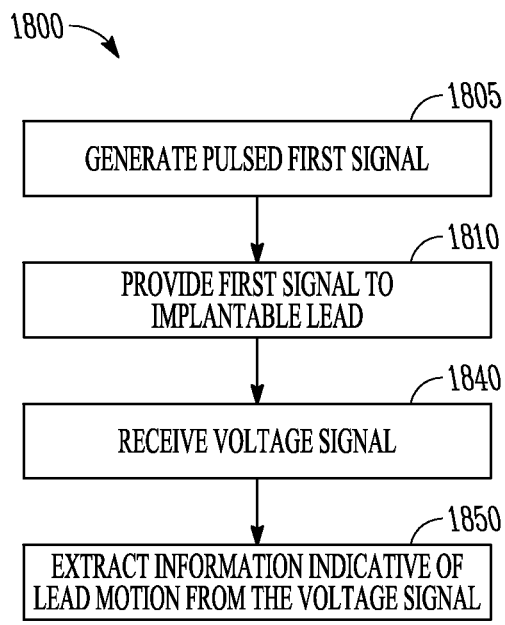
FIG. 18 illustrates generally an example that can include generating a pulsed first signal, providing the first signal to an implantable lead, receiving a voltage, or extracting information indicative of lead motion from the received voltage.

FIG. 18 illustrates generally an example 1800 that can include generating a pulsed first signal, providing the first signal to an implantable lead, receiving a voltage, or extracting information indicative of lead motion, such as using circuitry or techniques discussed above with respect to FIGS. 10-14.

At 1805, a first signal can be generated by a pulse generator. In an example, the pulse generator can produce a sequence of square wave pulses, or pulses having one or more other specified levels, duty cycles, repetition rates, or the like.

At 1810, a first signal can be provided to an implantable lead 1050. In an example, a first signal can be received from the excitation circuit 1410 by the detection circuit 1420. The received first signal can be coupled to the multiplexer 1421 in detection circuit 1420. In an example, the multiplexer 1421 can be coupled to the implantable lead 1050 via the interconnect 1460 and the lead coupling 1070. In an example, the detection circuit 1420 can include a multiplexer 1421 that can control the coupling of the first signal to the implantable lead 1050. The multiplexer 1421 can also be configured to apply a first signal to the capacitive element 1425.

At 1840, a voltage signal can be received. In an example, the multiplexer 1421 can be configured to apply a first signal to the implantable lead 1050 for a specified duration of time. In an example, the voltage signal can include a first voltage measurement of the implantable lead after a specified duration of time. In an example, the multiplexer 1421 can be configured to apply a first signal to the capacitive element 1425 for a specified duration of time (e.g., to charge the capacitive element 1425). The voltage signal can include a second voltage measurement of the capacitive element 1425 after a specified duration of time.

At 1850, information can be extracted from one or more of the first or second voltage signals indicative of motion of an implantable lead 1050. In an example, the voltage signal can be compared to a specified threshold voltage, or one or more voltage signals can be compared to an array of threshold voltages.

FIG. 19 illustrates generally an example 1900 that can include generating a pulsed first signal, providing the pulsed first signal to a first capacitance, providing the pulsed first signal to a second capacitance, receiving a first voltage, receiving a second voltage, or extracting information indicative of lead motion.

At 1905, a first signal can be generated by a pulse generator. In an example, the pulse generator can produce pulses such as including one or more current or voltage pulses including pulses of a specified amplitude, duty cycle, or morphology, among other parameters.

At 1910, a first signal can be provided to a first capacitance. In an example, the first capacitance can be provided at least in part by the implantable lead 1050. In an example, the first signal can be received from the excitation circuit 1410 by the detection circuit 1420. The received first signal can be coupled to the multiplexer 1421 in the detection circuit 1420. The multiplexer 1421 can be coupled to the implantable lead 1050 via the interconnect 1460 and the lead coupling 1070. In an example, the detection circuit 1420 can operate the multiplexer 1421 to determine when a first signal can be applied to the implantable lead 1050.

At 1920, the first signal can be similarly provided to the second capacitance. For example, the second capacitance can be provided by the capacitive element 1425. In an example, the multiplexer 1421 can be coupled to the capacitive element 1425. In an example, the detection circuit 1420 can operate the multiplexer 1421 to controllably couple the first signal to the second capacitance. The capacitive element 1425 can be a discrete or distributed capacitor or a combination of capacitors providing a specified capacitance value, a second implantable lead, or an array of interconnected implantable leads or conductors, among others.

At 1930, a first voltage signal can be received. The first voltage signal can be a signal in response to the first signal. In an example, the first voltage signal can indicate, among other things, a charge level of the first capacitance or a first count of a number of pulses provided by the first signal.

At 1940, the second voltage signal can be received. The second voltage signal can be a signal in response to the first signal. In an example, the second voltage signal can indicate, among other things, a charge level of the second capacitance or a second count of a number of pulses provided by the first signal.

At 1950, information can be extracted from the first and second voltage signals indicative of motion of the implantable lead 1050. In an example, the first and second voltage signals can represent, respectively, a duration of respective first and second capacitor charge times. In this example, the first charge time can include an interval wherein the voltage across the first capacitance is between a lower voltage threshold and an upper voltage threshold. Similarly, the second charge time can include an interval wherein the voltage across the second capacitance is between the lower and upper voltage thresholds. In an example, information indicative of lead motion can be extracted by determining a relative indication of the first and second durations. For example, the first duration can be measured to be greater or lesser than the second duration. For example, the difference between the first and second durations can indicate the magnitude of the displacement of the implantable lead 1050, wherein the displacement causes a change in the first capacitance. In an example, when the first and second duration of a charge time are approximately equivalent, the relative indication of information can indicate that the implantable lead 1050 is stationary or otherwise at equilibrium.

In an example, the first voltage signal can represent a first count of a number of pulses provided to the first capacitance. Similarly, the second voltage signal can represent a second count of a number of pulses provided to the second capacitance. In an example, information indicative of lead motion can be extracted by determining a relative indication of the first and second counts. For example, the difference between the first and second counts can indicate the magnitude of the displacement of the implantable lead 1050, wherein the displacement causes a change in the first capacitance. In an example, when the first and second counts are approximately equivalent or unchanging, the relative indication of information can indicate that the implantable lead 1050 is stationary or otherwise at equilibrium.

Figure 20:
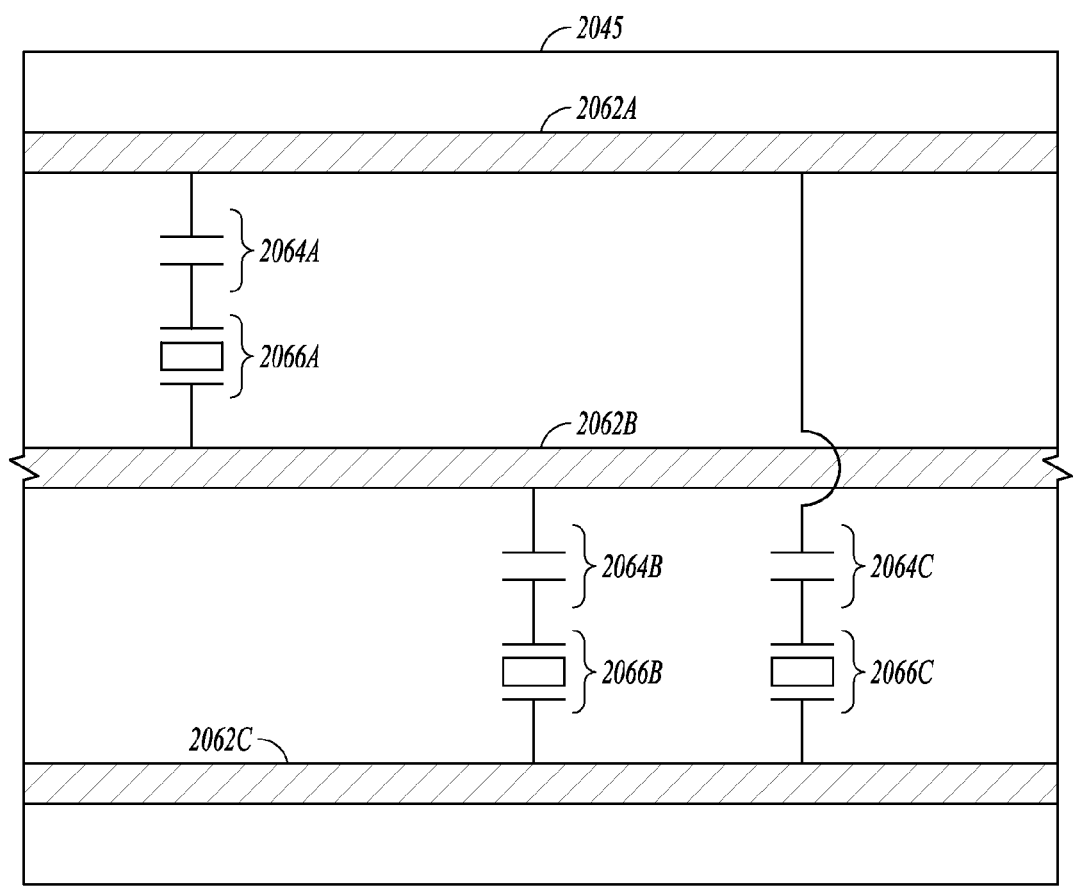
FIG. 20 illustrates generally an example of a portion of an implantable lead assembly that can include one or more transducers.

FIG. 20 illustrates generally an example of a portion of an implantable lead assembly 2045 that can include one or more piezoelectric transducers. In the example of FIG. 20, the implantable lead can include a first conductor 2062A, a second conductor 2062B, or a third conductor 2062C. A first transducer 2066A can be located on or within the lead assembly 2045, such as electrically coupled between the first conductor 2062A and the second conductor 2062B, such as including a first series capacitor 2064A (e.g., a DC-blocking capacitor). Similarly, a second transducer 2066B can be electrically coupled between the second conductor 2062B and the third conductor 2062C, such as via a second series capacitor 2064B. A third transducer 2066C can be electrically coupled between the first conductor 2062A and the third conductor 2062C, such as via a third series capacitor 2064C. Thus, in the example of FIG. 20, one or more of the transducers 2066A-C can be sampled or addressed via measurement or stimulation of a desired conductor pair (e.g., first and third conductors 2062A-C to address the third transducer 2066C, etc.).

In an example, one or more of the transducers 2066A-C can be excited such as to convert a non-therapeutic, non-stimulating electrical signal into acoustic energy (e.g., to provide acoustic energy such as ultrasonic energy). Conversely, one or more of the transducers 2066A-C can be configured for one or more of passive reception of acoustic energy (or mechanical vibration), or for reception of the acoustic transmission provided by another transducer, or the transducer being excited can modulate the excitation signal in response to received mechanical or acoustic energy. One or more of the conductors 2062A-C can be therapy delivery or cardiac electrical activity sensing conductors (e.g., the lead assembly 2045 need not carry extra conductors dedicated for use by the one or more transducers 2066A-C).

One or more of the transducers 2066A-C can include a piezoelectric construction, such as including metal or other conductive materials coupled to a lead-zirconate titanate material (PZT) piezoelectric material or coupled to a polyvinylidene fluoride (PVDF) piezoelectric material. For example, one or more of transducers 2066A-C can be used to measure blood velocity or other physiologic velocities relative to the transducer location, such as using a Doppler technique (e.g., a continuous-wave Doppler flow measurement). For example, a flow signal obtained using such techniques can include a high-frequency portion corresponding to the moving blood, a low frequency portion corresponding to heart wall motion, and a near-DC component such as corresponding to phase noise of an oscillator used to excite the transducer.

In an example, acoustic transmissions can be made between one of the transducers 2066A-C and another one of the transducers 2066A-C, such as to obtain information about a distance between various transducers 2066A-C. Such a distance can be determined via measurement of the time-delay between initiating an acoustic transmission at a first location and receiving a corresponding transmission at a second location. Thus, in the example of FIG. 20, such time-of-flight measurements can provide independent information about three different distances (e.g., between pairs of transducers 2066A-C, or between one or more of the transducers 2066A-C and another acoustic transmitter or receiver elsewhere), which can be tracked to reveal relative changes in displacement of portions of the implantable lead 2045. Multipath or other errors can be controlled or reduced such as by time-gating the received acoustic energy such as to capture the first (e.g., direct) or other desired time-of-flight between a desired transmit-receive transducer pair.

The selection of piezoelectric materials and operating frequency ranges can include considerations of size or mechanical flexibility, or directivity of resulting acoustic (e.g., ultrasonic) transmission or reception. For example, the frequency can be selected to be high enough that the corresponding acoustic wavelength is small with respect to the dimensions of the transducer, providing more omni-directional transmission or reception of acoustic energy.

In an example, the one or more transducers 2066A-C can be addressed using a frequency-selective technique. For example, a resonant device such as a thickness-mode PZT device can be excited with a burst of electrical energy corresponding to the PZT device's resonant frequency. Two or more transducers can be placed parallel to each other electrically, such as at specified locations along the implantable lead assembly 2045, such as including staggered or offset resonant frequencies, such as to provide spatially-addressable transducers that can be addressed using a desired frequency range corresponding to the resonant of a desired transducer at a specified location.

In an example, one or more of the transducers 2066A-C need not be resonant. For example, non-resonant PVDF transducers can be used interchangeably for transmission or reception of acoustic energy. In an example, a narrow-band PZT transmitting transducer can be used, and a broadband PVDF receiving transducer can be used. In this manner, the PVDF receiver need not be carefully matched or tuned to the PZT transmitter.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus including an implantable medical device, the implantable medical device (IMD) comprising:
   a receiver circuit, configured to be electrically coupled to an implantable lead, the receiver circuit configured to receive a response to an excitation signal applied to a conductor in the lead, the response modulated according to a change in an electrical characteristic of at least one conductor in the lead to provide information indicative of a movement of the implantable lead, the movement due at least in part to a motion of a heart;

an arrhythmia detection circuit configured to determine an arrhythmia status using the response information indicative of the movement of the implantable lead; and an arrhythmia classification circuit, coupled to the arrhythmia detection circuit, the arrhythmia classification circuit configured to determine one or more of a location or a type of an arrhythmia, using the response information indicative of the movement of the implantable lead, in response to the arrhythmia detection circuit determining an arrhythmia status indicating that an arrhythmia is occurring or has occurred.

2. The apparatus of claim 1, wherein the arrhythmia classification circuit is configured to determine the location of the arrhythmia.

3. The apparatus of claim 1, wherein the arrhythmia classification circuit is configured to determine the type of the arrhythmia.

4. The apparatus of claim 1, wherein the IMD comprises an excitation circuit configured to provide a non-tissue stimulating, non-therapeutic electrical excitation signal to the implantable lead, the signal comprising a time varying signal including a first range of frequencies.

5. The apparatus of claim 4, wherein the information indicative of a movement of the implantable lead includes one or more of magnitude information, or phase information, corresponding to one or more frequencies included in the first range of frequencies, the magnitude information, or phase information, determined at least in part using an electrical response signal provided by the implantable lead in response to the excitation signal and the movement of the implantable lead.

6. The apparatus of claim 5, wherein one or more of the magnitude information, or the phase information, includes a time-varying portion corresponding to the movement of the implantable lead.

7. The apparatus of claim 1, further comprising an implantable lead configured to be located within or near the heart, the implantable lead including an electrode configured to provide one or more of electrostimulation to the heart or to sense cardiac electrical activity.

8. The apparatus of claim 7, wherein the implantable lead comprises a piezoelectric acoustic transducer configured to receive acoustic information indicative of the movement of the implantable lead, the piezoelectric acoustic transducer coupled to a conductor included in the implantable lead.

9. The apparatus of claim 1, wherein the arrhythmia classification circuit is configured to determine one or more of an arrhythmia type or arrhythmia location using morphology information or interval information indicative of lead movement corresponding to successive cardiac cycles.

10. The apparatus of claim 1, wherein the IMD comprises a sensing circuit configured to obtain information indicative of cardiac electrical activity, the sensing circuit coupled to the arrhythmia detection circuit; and wherein the arrhythmia detection circuit is configured to determine an arrhythmia status using the information indicative of the movement of the implantable lead and information obtained via the sensing circuit.

11. The apparatus of claim 1, wherein the receiver circuit is configured to obtain information indicative of lead motion from at least two different locations within or near the heart; and wherein the arrhythmia classification circuit is configured to determine the one or more of the type or location of the arrhythmia using information about the location of lead motion.

12. The apparatus of claim 11, further comprising a first lead located within or near a first location of the heart; and a second lead located within or near a second location of the heart.

13. The apparatus of claim 1, comprising a therapy generation circuit, coupled to the arrhythmia classification circuit, the therapy generation circuit configured to provide a therapy in response to information about at least one of the arrhythmia status or the location or the type of an arrhythmia.

14. The apparatus of claim 13, wherein the therapy generation circuit is configured to be inhibited from generating an arrhythmia therapy when the information about at least one of the arrhythmia status or the location or the type of an arrhythmia indicates that an arrhythmia is one or more of supraventricular in origin or hemodynamically stable.

15. The apparatus of claim 1, wherein the arrhythmia detection circuit is configured to determine interval information about one or more time intervals between successive cardiac contractions; and wherein the arrhythmia detection circuit is configured to determine an arrhythmia status using the interval information.

16. An implantable medical device (IMD) including a processor-readable medium comprising instructions that, when executed by the processor, cause the IMD to:

obtain a response to an excitation signal applied to a conductor in an implantable lead, the response modulated according to a change in an electrical characteristic of at least one conductor in the lead to provide information indicative of a movement of the implantable lead, the movement due at least in part to a motion of a heart;

determine an arrhythmia status using the response information indicative of the movement of the implantable lead; and determine one or more of a location or a type of an arrhythmia, using the response information indicative of the movement of the implantable lead, in response to the determined arrhythmia status indicating that an arrhythmia is occurring or has occurred.

17. The IMD of claim 16, wherein the processor readable medium comprises instructions that, when executed by the processor, cause the IMD to determine a location of an arrhythmia, using the information indicative of the movement of the implantable lead, in response to the determination that an arrhythmia is occurring or has occurred.

18. The IMD of claim 16, wherein the processor readable medium comprises instructions that, when executed by the processor, cause the IMD to determine a type of an arrhythmia, using the information indicative of the movement of the implantable lead, in response to the determination that an arrhythmia is occurring or has occurred.

19. The IMD of claim 16, wherein the processor readable medium comprises instructions that, when executed by the processor, cause the IMD to:

determine interval information about one or more time intervals between successive cardiac contractions; and determine the arrhythmia status using the interval information.

20. The IMD of claim 16, wherein the processor-readable medium comprises instructions that, when executed by the processor, cause the IMD to determine one or more of an arrhythmia type or an arrhythmia location using morphology information or interval information indicative of lead movement corresponding to successive cardiac cycles.

21. The IMD of claim 16, wherein the processor-readable medium comprises instructions that, when executed by the processor, cause the IMD to:

obtain information indicative of cardiac electrical activity; and determine an arrhythmia status using the information indicative of the movement of the implantable lead and the information indicative of cardiac electrical activity.

22. The IMD of claim 16, wherein the processor-readable medium comprises instructions that, when executed by the processor, cause the IMD to provide an arrhythmia therapy using a therapy generation circuit in response to information about at least one of the arrhythmia status or the one or more of the location or the type of the arrhythmia.

23. The IMD of claim 22, wherein the processor-readable medium comprises instructions that, when executed by the processor, cause the IMD to inhibit generation of the arrhythmia therapy by the therapy generation circuit when the arrhythmia classification information indicates that an arrhythmia is one or more of supraventricular in origin or hemodynamically stable.

24. An apparatus including an implantable medical device, the implantable medical device (IMD) comprising:

a means of receiving, via an electrical coupling of an implantable lead to the IMD, a response to an excitation signal applied to a conductor of the implantable lead, the response modulated according to a change in an electrical characteristic of at least one conductor in the lead to provide information indicative of a movement of the implantable lead, the movement due at least in part to a motion of a heart;

a means of determining an arrhythmia status using the response information indicative of the movement of the implantable lead; and a means of determining one or more of a location or a type of an arrhythmia, using the response information indicative of the movement of the implantable lead, in response to the determined arrhythmia status indicating that an arrhythmia is occurring or has occurred.

* * * * *